US007132508B2

(12) United States Patent
Dairaghi et al.

(10) Patent No.: US 7,132,508 B2
(45) Date of Patent: Nov. 7, 2006

(54) MAMMALIAN CHEMOKINE REAGENTS

(75) Inventors: Daniel J. Dairaghi, Palo Alto, CA (US); Takahiko Hara, Ingagun Chiba (JP); Atsushi Miyajima, Tokyo (JP); Thomas J. Schall, Menlo Park, CA (US); Wei Wang, Palo Alto, CA (US); Akihiko Yoshimura, Kurume (JP)

(73) Assignee: Schering Corporation, Kenilworth, NJ (US)

( * ) Notice: Subject to any disclaimer, the term of this patent is extended or adjusted under 35 U.S.C. 154(b) by 276 days.

(21) Appl. No.: 10/293,050

(22) Filed: Nov. 13, 2002

(65) Prior Publication Data

US 2003/0130494 A1 Jul. 10, 2003

Related U.S. Application Data

(62) Division of application No. 08/567,882, filed on Dec. 8, 1995, now Pat. No. 6,512,103.

(51) Int. Cl.

*C07K 14/00* (2006.01)
*A16K 39/395* (2006.01)
*A16K 38/19* (2006.01)
*C07K 1/00* (2006.01)
*G01N 33/567* (2006.01)

(52) U.S. Cl. ................. 530/351; 530/300; 530/388.23; 530/350; 530/380; 530/395; 530/391.3; 435/7.21; 435/69.5; 435/252.3; 435/320.1; 436/501; 424/130.1; 424/178.1; 424/85.1

(58) Field of Classification Search ................ 530/300, 530/350, 388.22; 536/23.5; 435/6, 7.1, 435/7.21, 69.1, 69.5, 252.3, 320.1
See application file for complete search history.

(56) References Cited

U.S. PATENT DOCUMENTS 5,504,003 A * 4/1996 Li et al. .................. 435/365.1
5,770,402 A 6/1998 Beutler et al.

FOREIGN PATENT DOCUMENTS

WO WO 96/22371 7/1996
WO WO 96/34891 11/1996

OTHER PUBLICATIONS

Benjamini-E et al., eds, Immunology : A Short Course (1988).*
Alexander et al., Proc. Natl. Acad. Sci. 89(3352-3356)1992.*
Sticht et al. Biochemistry 38(5995-6002)1999.*
Pardigol et al., PNAS 95(6308-6313)98.*
Bacon et al., "IL-8-induced signal transduction in T lymphocytes involves receptor-mediated activation of phospholipases C and D," *J Immunol*, 154(8):3654-3666 (1995).
Bacon et al., "Contrasting in vitro lymphocyte chemotactic activity of the hydroxyl enantiomers of 12-hydroxy-5,8,10,14-eicosatetraenoic acid," *Br J Pharmacol*, 95(3):966-974 (1988).
Berger et al., "The gene for C10, a member of the β-chemokine family, is located on mouse chromosome 11 and contains a novel second exon not found in other chemokines," *DNA Cell Biol*, 12(9):839-847 (1993).
Berridge, "Inositol triphosphate and calcium signaling," *Nature*, 361(6410):315-325 (1993).
Billah and Anthes, "The regulation and cellular functions of phosphatidylcholine hydrolysis," *Biochem J*, 269(2):281-291 (1990).
Danoff et al., "Cloning, genomic organization, and chromosomal localization of the *Scya5*gene encoding the murine chemokine Rantes," *J Immunol*, 152(3):1182-1189 (1994).
Groneborn and Clore, "Modeling the three-dimensional structure of the monocyte chemo-attractant and activating protein MCAF/MCP-1 on the basis of the solution structure of interleukin-8" *Protein Eng*, 4(3):263-269 (1991).
Hara et al., "Molecular cloning and functional characterization of a novel member of the C-C chemokine family," *J Immunol*, 155(11):5352-5358 (1995).
Kelner et al., "Lymphotactin: a cytokine that represents a new class of chemokine," *Science*, 266(5189):1395-1399 (1994).
Lodi et al., "High-resolution solution structure of the beta chemokine hMIP- beta by multidimensional NMR," *Science*, 263(5154):1762-1767 (1994).
Matsushima and Oppenheim, "Interleukin 8 and MCAF: novel inflammatory cytokines inducible by IL 1 and TNF, " *Cytokine*, 1(1):2-13 (1989).
Miller and Krangel, "The human cytokine I-309 is a monocyte chemoattractant," *Proc Natl Acad Sci USA*, 89(7):2950-2954 (1992).
Miller et al., "Biology and biochemistry of the chemokines: a family of chemotactic and inflammatory cytokines," *Crit Rev Immunol*, 12(1-2):17-46 (1992).
Oppenheim et al., "Properties of the novel proinflammatory supergene 'intercrine' cytokine family," *Annu Rev Immunol*, 9:617-648 (1991).
Orlofsky et al., "Selective induction of the beta chemokine C10 by IL-4 in mouse macrophages," *J Immunol*, 152(10):5084-5091 (1994).
Thompson (Ed.), *The Cytokine Handbook*, Schall, "The Chemokines," pp. 419-460, 2nd ed., The Academic Press Inc., San Diego, CA (1994).
Schall and Bacon, "Chemokines, leukocyte trafficking, and inflammation," *Curr Opin Immunol*, 6(6):865-873 (1994).
Schall, "Biology of the Rantes/Sis cytokine family," *Cytokine*, 3(3):165-183 (1991).
Schall et al., "Human macrophage inflammatory protein alpha (MIP-1 alpha) and MIP-1 beta chemokines attract distinct populations of lymphocytes," *J Exp Med*, 177(6):1821-1826 (1993).
Stoeckle and Barker, "Two-burgeoning families of platelet factor 4-related proteins: mediators of the inflammatory response," *New Biol*, 2(4):313-323 (1990).

(Continued)

*Primary Examiner*—Elizabeth Kemmerer
*Assistant Examiner*—Michael Brannock
(74) *Attorney, Agent, or Firm*—Thomas A. Triolo

(57) ABSTRACT

A novel CC chemokine which is from a mammal, reagents related thereto including purified proteins, specific antibodies, and nucleic acids encoding said chemokine. A chemokine receptor is also provided. Methods of using said reagents and diagnostic kits are also provided.

8 Claims, No Drawings

OTHER PUBLICATIONS

Wilson et al., "Clustering of cytokine genes on mouse chromosome 11," *J Exp Med*, 171(4):1301-1314 (1990).

Neote et al., "Molecular cloning, functional expression, and signaling characteristics of a C-C chemokine receptor," *Cell*, 72(3):415-425 (1993).

Hillier et al., *GenBank*, Accession No. R91733, Aug. 25, 1995. The WashU-Merck EST project.

Hillier et al., *GenBank*, Accession No. R96668, Sep. 11, 1995. The WashU-Merck EST project.

Hillier et al., *GenBank*, Accession No. H62013, Oct. 6, 1995. The WashU-Merck EST project.

Hillier et al., *GenBank*, Accession No. H54642, Sep. 21, 1995. The WashU-Merck EST project.

Poltorak et al., "MIP-1-gamma: molecular cloning, expression, and biological activities of a novel CC chemokine that is constitutively secreted *in vivo,*" *J Inflamm*, 45(3):207-219 (1995).

Combadiere et al., "Cloning and functional expression of a human eosinophil CC chemokine receptor," *J Biol Chem*, 270(28)16491-16494 (1995).

Poltorak et al., "MIP-1-gamma: a novel neutrophil-activating, pyrogenic CC chemokine that circulates in plasma at pharmacologically active concentrations," *J Invest Med*, 43(Suppl 2):364A (1995).

Poltorak et al., "Molecular cloning of MIP-1-gamma, a new member of the chemokine family, through differential screening based on extinction of macrophage-specific genes," *Clin Res*, 42(2):306A (1994).

Youn et al., "A novel chemokine, macrophage inflammatory protein-related protein-2, inhibits colony formation of bone marrow myeloid progenitors," *J Immunol*, 155(5):2661-2667 (1995).

Pardigol et al., "HCC-2, a human chemokine: gene structure , expression pattern, and biological activity," *Proc Natl Acad Sci USA*, 95(11):6308-6313 (1998).

*Derwent Geneseq Patent Sequence Database*, Accession No. 97P-W25941, citing: WO 9721812 A2 dated 970619; US 95-567882 dated 951208; "Search record pertaining to human CCF-18, performed in Jul. 1998".

*Derwent Geneseq Patent Sequence Database*, Accession No. 97P-W07202, citing: WO 9634891 A1 dated 961107; US 95-446881 dated 950505; "Search record pertaining to human CCF-18, performed in Jul. 1998".

*Derwent Geneseq Patent Sequence Database*, Accession No. 96P-W05186, citing: WO 9632481 A1 dated 961017; US 95-42114 dated 950413; "Search record pertaining to human CCF-18, performed in Jul. 1998".

*Derwent Geneseq Patent Sequence Database*, Accession No. 96P-W38170, citing: WO 9741230 A2 dated 971106; DE 96-19617312 dated 960430; "Search record pertaining to human CCF-18, performed in Jul. 1998".

*Derwent Geneseq Patent Sequence Database*, Accession No. 97P-W25942, citing: WO 9721812 A2 dated 970619; US 95-567882 dated 951208; "Search record pertaining to human CCF-18, performed in Jul. 1998".

*Derwent Geneseq Patent Sequence Database*, Accession No. 97P-W38170, citing: WO 9741230 A2 dated 971106; DE 96-19617312 dated 960430; "Search record pertaining to mouse CCF-18, performed in Jul. 1998".

*Derwent Geneseq Patent Sequence Database*, Accession No. 97P-W25942, citing: WO 9721812 A2 dated 970619; US 95-567882 dated 951208; "Search record pertaining to mouse CCF-18, performed in Jul. 1998".

*Derwent Geneseq Patent Sequence Database*, Accession No. 96P-W07202, citing: WO 9634891, A1 dated 961107; US 95-446881 dated 950505; "Search record pertaining to human CCF-18, performed in Jul. 1998".

*Derwent Geneseq Patent Sequence Database*, Accession No. 96P-W05186, citing: WO 9632481 A1 dated 961017; US 95-421144 dated 950413; "Search record pertaining to human CCF-18, performed in Jul. 1998".

*Derwent Geneseq Patent Sequence Database*, Accession No. 95P-R76126, citing: WO 9517092 A1 dated 950629; US 94-208339 dated 940308; "Search record pertaining to mouse CCF-18, performed in Jul. 1998".

*Derwent Geneseq Patent Sequence Database*, Accession No. 97P-W17663, citing: WO 9715594 A1 dated 970501; US 95-6051 dated 951024; "Search record pertaining to human CCF-18, performed in Jul. 1998".

*Derwent Geneseq Patent Sequence Database*, Accession No. 97P-W16315, citing: WO 9712041 A1 dated 970403; US 95-4517, dated 950929; "Search record pertaining to human CCF-18, performed in Jul. 1998".

*Derwent Geneseq Patent Sequence Database*, Accession No. 97P-W31850, citing: WO 9741154 A1 dated 971106; GB 97-894 dated 970117; US 96-16158 dated 960426; US 96-17113 dated 960426; "Search record pertaining to CCR3 (segment 1), performed in Jun. 1998".

*Derwent Geneseq Patent Sequence Database*, Accession No. 97P-W27124, citing: WO 9722698 A2 dated 970626; US 96-661393 dated 960607; US 95-575967 dated 951220; "Search record pertaining to CCR3 (segment 1), performed in Jun. 1998".

*Derwent Geneseq Patent Sequence Database*, Accession No. 97P-W25943, citing: WO 9721812 A2 dated 970619; US 95-567882 dated 951208 "Search record pertaining to CCR3 (segment 1), performed in Jun. 1998".

*Derwent Geneseq Patent Sequence Database*, Accession No. 97P-W10100, citing: WO 9700960 A1 dated 970109; US 95-494093 dated 950623; "Search record pertaining to CCR3 (segment 1), performed on Jun. 28, 1998".

*Derwent Geneseq Patent Sequence Database*, Accession No. 96P-W03378, citing: WO 9622371 A2 dated 960725; US 95-375199 dated 950119; "Search record pertaining to CCR3 (segment 1), performed in Jun. 1998".

*Derwent Geneseq Patent Sequence Database*, Accession No. 96P-W03377, citing: WO 9622371 A2 dated 960725; US 95-375199 dated 950119; "Search record pertaining to CCR3 (segment 1), performed in Jun. 1998".

*Derwent Geneseq Patent Sequence Database*, Accession No. 96P-W03376, citing: WO 9622371 A2 dated 960725; US 95-375199 dated 950119; "Search record pertaining to CCR3 (segment 1), performed in Jun. 1998".

*Derwent Geneseq Patent Sequence Database*, Accession No. 97P-W26588, citing: US 5652133 A dated 970729; US 93-12988 dated 930128; "Search record pertaining to CCR3 (segment 1), performed in Jun. 1998".

*Derwent Geneseq Patent Sequence Database*, Accession No. 97P-W25751, citing: JP 09176048 A dated 970708; and JP 95-342130 dated 951228; "Search record pertaining to CCR3 (segment 1), performed in Jun. 1998".

*Derwent Geneseq Patent Sequence Database*, Accession No. 94P-R52749, citing: WO 9411504 A dated 940526; WO 93-U100672 dated 931104; US 92-974025 dated 921110; "Search record pertaining to CCR3 (segment 1), performed in Jun. 1998".

*Derwent Geneseq Patent Sequence Database*, Accession No. 97P-W25943, citing: WO 9721812 A2 dated 970619; WO 96-US19139 dated 961205; US 95-567882 dated 951208; "Search record pertaining to CCR3 (segment 2), performed in Jun. 1998".

*Derwent Geneseq Patent Sequence Database*, Accession No. 97P-W31850, citing: WO 9741154 A1 dated 971106; WO 96-US6568 dated 970424; GB 97-894 dated 970117; US 96-16158 dated 960426; US 96-17113 dated 960426; "Search record pertaining to CCR3 (segment 2), performed in Jun. 1998".

*Derwent Geneseq Patent Sequence Database*, Accession No. 97P-W27124, citing: WO 9722698 A2 dated 970626; WO 96-U200759 dated 961220; US 96-661393 dated 960607; US 95-575967 dated 951220; "Search record pertaining to CCR3 (segment 2), performed in Jun. 1998".

*Derwent Geneseq Patent Sequence Database*, Accession No. 96P-W03377, citing: WO 9622371 A2 dated 960725; WO 96-US608 dated 960119; US 95-375199 dated 950119; "Search record pertaining to CCR3 (segment 2), performed in Jun. 1998".

*Derwent Geneseq Patent Sequence Database*, Accession No. 97P-W10100, citing: WO 9700960 A1 dated 970109; WO 96-US10723 dated 960621; US 95-494093 dated 950623; "Search record pertaining to CCR3 (segment 2), performed in Jun. 1998".

*Derwent Geneseq Patent Sequence Database*, Accession No. 96P-W03376, citing: WO 9622371 A2 dated 960725; WO 96-US608 dated 960119; US 95-375199 dated 950119; "Search record pertaining to CCR3 (segment 2), performed in Jun. 1998".

*Derwent Geneseq Patent Sequence Database*, Accession No. 96P-W03378, citing: WO 9622371 A2 dated 960725; WO 96-US608 dated 960119; US 95-375199 dated 950119; "Search record pertaining to CCR3 (segment 2), performed in Jun. 1998".

*Derwent Geneseq Patent Sequence Database*, Accession No. 97P-W26588, citing: US 5652133 A dated 970729; US 93-12988 dated 930128; US 93-12988 dated 930128; "Search record pertaining to CCR3 (segment 2), performed in Jun. 1998".

*Derwent Geneseq Patent Sequence Database*, Accession No. 97P-W25751, citing: JP 09176048 A dated 970708; JP 95-342130 dated 951228; JP 95-342130 dated 951228; "Search record pertaining to CCR3 (segment 2), performed in Jun. 1998".

*Derwent Geneseq Patent Sequence Database*, Accession No. 94P-R52749, citing: WO 9411504 A dated 940526; WO 93-U100672 dated 931104; US 92-974025 dated 921110; "Search record pertaining to CCR3 (segment 2), performed in Jun. 1998".

*Derwent Geneseq Patent Sequence Database*, Accession No. 97P-W31850, citing: WO 9741154 A1 dated 971106; WO 97-US6568 dated 970424; GB 97-894 dated 970117; US 96-16158 dated 960426; US 96-17113 dated 960426; "Search record pertaining to CCR3 (segment 3), performed in Jun. 1998".

*Derwent Geneseq Patent Sequence Database*, Accession No. 97P-W27124, citing: WO 9722698 A2 dated 970626; WO 96-U200759 dated 961220; US 96-661393 dated 960607; US 95-575967 dated 951220; "Search record pertaining to CCR3 (segment 3), performed in Jun. 1998".

*Derwent Geneseq Patent Sequence Database*, Accession No. 97P-W25943, citing: WO 9721812 A2 dated 970619; WO 96-US19139 dated 961205; US 95-567882 dated 951208; "Search record pertaining to CCR3 (segment 3), performed in Jun. 1998".

*Derwent Geneseq Patent Sequence Database*, Accession No. 97P-W10100, citing: WO 9700960 A1 dated 970109; WO 96-US10723 dated 960621; US 95-494093 dated 950623; "Search record pertaining to CCR3 (segment 3), performed in Jun. 1998".

*Derwent Geneseq Patent Sequence Database*, Accession No. 96P-W03377, citing: WO 9622371 A2 dated 960725; WO 96-US608 dated 960119; US 95-375199 dated 950119; "Search record pertaining to CCR3 (segment 3), performed in Jun. 1998".

*Derwent Geneseq Patent Sequence Database*, Accession No. 96P-W03376, citing: WO 9622371 A2 dated 960725; WO 96-US608 dated 960119; US 95-375199 dated 950119; "Search record pertaining to CCR3 (segment 3), performed in Jun. 1998".

*Derwent Geneseq Patent Sequence Database*, Accession No. 96P-W03378, citing: WO 9622371 A2 dated 960725; WO 96-US608 dated 960608; US 95-375199 dated 950119; "Search record pertaining to CCR3 (segment 3), performed in Jun. 1998".

*Derwent Geneseq Patent Sequence Database*, Accession No. 97P-W26588, citing: US 5652133 A dated 970729; US 93-12988 dated 930128; US 93-12988 dated 930128; "Search record pertaining to CCR3 (segment 3), performed in Jun. 1998".

*Derwent Geneseq Patent Sequence Database*, Accession No. 97P-W25751, citing: JP 09176048 A dated 970708; JP 95-342130 dated 951228; JP 95-342130 dated 951228; "Search record pertaining to CCR3 (segment 3), performed in Jun. 1998".

*Derwent Geneseq Patent Sequence Database*, Accession No. 94P-R52749, citing: WO 9411504 A dated 940526; WO 93-U100672 dated 931104; US 92-974025 dated 921110; "Search record pertaining to CCR3 (segment 3), performed in Jun. 1998".

GenBank Accession No. AAK49027, May 2, 2001.

Sticht et al., "Solution structure of the human CC chemokine 2: A monomeric representative of the CC chemokine subtype," *Biochemistry*, 38(19):5995-6002 (1999).

* cited by examiner

SEQUENCE LISTING

<160> NUMBER OF SEQ ID NOS: 9

<210> SEQ ID NO 1
<211> LENGTH: 1165
<212> TYPE: DNA
<213> ORGANISM: Mus sp.
<220> FEATURE:
<221> NAME/KEY: CDS

-continued

```
<222> LOCATION: (53)..(421)
<223> OTHER INFORMATION:

<400> SEQUENCE: 1

gcctcgtgcc gaattcggca cgaggggcca gctgggtctg cccactaaga ag atg aag      58
                                                         Met Lys
                                                         1

cct ttt cat act gcc ctc tcc ttc ctc att ctt aca act gct ctt gga       106
Pro Phe His Thr Ala Leu Ser Phe Leu Ile Leu Thr Thr Ala Leu Gly
        5                   10                  15

atc tgg gcc cag atc aca cat gca aca gag aca aaa gaa gtc cag agc       154
Ile Trp Ala Gln Ile Thr His Ala Thr Glu Thr Lys Glu Val Gln Ser
    20                  25                  30

agt ctg aag gca cag caa ggg ctt gaa att gaa atg ttt cac atg ggc       202
Ser Leu Lys Ala Gln Gln Gly Leu Glu Ile Glu Met Phe His Met Gly
35                  40                  45                  50

ttt caa gac tct tca gat tgc tgc ctg tcc tat aac tca cgg att cag       250
Phe Gln Asp Ser Ser Asp Cys Cys Leu Ser Tyr Asn Ser Arg Ile Gln
                55                  60                  65

tgt tca aga ttt ata ggt tat ttt ccc acc agt ggt ggg tgt acc agg       298
Cys Ser Arg Phe Ile Gly Tyr Phe Pro Thr Ser Gly Gly Cys Thr Arg
            70                  75                  80

ccg ggc atc atc ttt atc agc aag agg ggg ttc cag gtc tgt gcc aac       346
Pro Gly Ile Ile Phe Ile Ser Lys Arg Gly Phe Gln Val Cys Ala Asn
        85                  90                  95

ccc agt gat cgg aga gtt cag aga tgc att gaa aga ttg gag caa aac       394
Pro Ser Asp Arg Arg Val Gln Arg Cys Ile Glu Arg Leu Glu Gln Asn
    100                 105                 110

tca caa cca cgg acc tac aaa caa taa catttgcttg aagagaaggg             441
Ser Gln Pro Arg Thr Tyr Lys Gln
115                 120

tgtgaactgc cagctacttt ctttggtctt ccccagtgac cacctaagcg gctctaagtg    501

tttattttta taggtatata aacatttttt tttctgttcc actttaaagt ggcatatctg    561

gctttgtcac agaggggaaa cttgtctgtg ccaaccccag tcatctgaaa actcagatgc    621

ctgcggaagg tctgaagctg actcaatgac tacacataat atttgattga gataaatggg    681

caaggtctgg agagatggct tggtggttaa gagcacctgc tgctcttcca gaggacctgg    741

gttcaattcc cacttagatg gcagctcaaa ctatctataa ttccaattcc aaagaaaact    801

gatgccctat tttgcccttt agttagtagt atttacagta ttctttataa attcaccttg    861

acatgaccat cttgagctac agccatccta actgcctcag aatcactcaa gttcttccac    921

tcggtttccc agcggattat aagtggataa actgtgagag tggtctgtgg gactttggaa    981

tgtgtctggt tctgatagtc acttatggca acccgggtac attcaactag gatgaaataa   1041

attctgcctt agcccagtag tatgtctgtg tttgtaagga cccagctgat tttcccacca   1101

cccctccatc agtaagccac taataaagtg catctatgca gccaaaaaaa aaaaaaaaaa   1161

aaaa                                                                1165


<210> SEQ ID NO 2
<211> LENGTH: 122
<212> TYPE: PRT
<213> ORGANISM: Mus sp.

<400> SEQUENCE: 2

Met Lys Pro Phe His Thr Ala Leu Ser Phe Leu Ile Leu Thr Thr Ala
1               5                   10                  15

Leu Gly Ile Trp Ala Gln Ile Thr His Ala Thr Glu Thr Lys Glu Val
```

```
            20                  25                  30

Gln Ser Ser Leu Lys Ala Gln Gln Gly Leu Glu Ile Glu Met Phe His
        35                  40                  45

Met Gly Phe Gln Asp Ser Ser Asp Cys Cys Leu Ser Tyr Asn Ser Arg
    50                  55                  60

Ile Gln Cys Ser Arg Phe Ile Gly Tyr Phe Pro Thr Ser Gly Gly Cys
65                  70                  75                  80

Thr Arg Pro Gly Ile Ile Phe Ile Ser Lys Arg Gly Phe Gln Val Cys
                85                  90                  95

Ala Asn Pro Ser Asp Arg Arg Val Gln Arg Cys Ile Glu Arg Leu Glu
            100                 105                 110

Gln Asn Ser Gln Pro Arg Thr Tyr Lys Gln
        115                 120


<210> SEQ ID NO 3
<211> LENGTH: 348
<212> TYPE: DNA
<213> ORGANISM: Homo sapiens
<220> FEATURE:
<221> NAME/KEY: CDS
<222> LOCATION: (1)..(342)
<223> OTHER INFORMATION:

<400> SEQUENCE: 3

atg aag gtc tcc gtg gct gcc ctc tcc tgc ctc atg ctt gtt gct gtc       48
Met Lys Val Ser Val Ala Ala Leu Ser Cys Leu Met Leu Val Ala Val
1               5                   10                  15

ctt gga tcc cag gcc cag ttc ata aat gat gca gag aca gag tta atg       96
Leu Gly Ser Gln Ala Gln Phe Ile Asn Asp Ala Glu Thr Glu Leu Met
            20                  25                  30

atg tca aag ctt cca ctg gaa aat cca gta gtt ctg aac agc ttt cac      144
Met Ser Lys Leu Pro Leu Glu Asn Pro Val Val Leu Asn Ser Phe His
        35                  40                  45

ttt gct gct gac tgc tgc acc tcc tac atc tca caa agc atc ccg tgt      192
Phe Ala Ala Asp Cys Cys Thr Ser Tyr Ile Ser Gln Ser Ile Pro Cys
    50                  55                  60

tca ctc atg aaa agt tat ttt gaa acg agc agc gag tgc tcc aag cca      240
Ser Leu Met Lys Ser Tyr Phe Glu Thr Ser Ser Glu Cys Ser Lys Pro
65                  70                  75                  80

ggt gtc ata ttc ctc acc aag aag ggg cgg caa gtc tgt gcc aaa ccc      288
Gly Val Ile Phe Leu Thr Lys Lys Gly Arg Gln Val Cys Ala Lys Pro
                85                  90                  95

agt ggt ccg gga gtt cag gat tgc atg aaa aag ctg aag ccc tac tca      336
Ser Gly Pro Gly Val Gln Asp Cys Met Lys Lys Leu Lys Pro Tyr Ser
            100                 105                 110

ata taa taataa                                                       348
Ile


<210> SEQ ID NO 4
<211> LENGTH: 113
<212> TYPE: PRT
<213> ORGANISM: Homo sapiens

<400> SEQUENCE: 4

Met Lys Val Ser Val Ala Ala Leu Ser Cys Leu Met Leu Val Ala Val
1               5                   10                  15

Leu Gly Ser Gln Ala Gln Phe Ile Asn Asp Ala Glu Thr Glu Leu Met
            20                  25                  30

Met Ser Lys Leu Pro Leu Glu Asn Pro Val Val Leu Asn Ser Phe His
        35                  40                  45
```

```
Phe Ala Ala Asp Cys Cys Thr Ser Tyr Ile Ser Gln Ser Ile Pro Cys
    50                  55                  60

Ser Leu Met Lys Ser Tyr Phe Glu Thr Ser Ser Glu Cys Ser Lys Pro
65                  70                  75                  80

Gly Val Ile Phe Leu Thr Lys Lys Gly Arg Gln Val Cys Ala Lys Pro
                85                  90                  95

Ser Gly Pro Gly Val Gln Asp Cys Met Lys Lys Leu Lys Pro Tyr Ser
            100                 105                 110

Ile


<210> SEQ ID NO 5
<211> LENGTH: 769
<212> TYPE: DNA
<213> ORGANISM: Homo sapiens
<220> FEATURE:
<221> NAME/KEY: misc_feature
<222> LOCATION: (315)..(315)
<223> OTHER INFORMATION: n = any nucleotide
<220> FEATURE:
<221> NAME/KEY: misc_feature
<222> LOCATION: (410)..(410)
<223> OTHER INFORMATION: n = any nucleotide
<220> FEATURE:
<221> NAME/KEY: misc_feature
<222> LOCATION: (567)..(567)
<223> OTHER INFORMATION: n = any nucleotide
<220> FEATURE:
<221> NAME/KEY: misc_feature
<222> LOCATION: (568)..(568)
<223> OTHER INFORMATION: n = any nucleotide
<220> FEATURE:
<221> NAME/KEY: misc_feature
<222> LOCATION: (601)..(601)
<223> OTHER INFORMATION: n = any nucleotide
<220> FEATURE:
<221> NAME/KEY: misc_feature
<222> LOCATION: (615)..(615)
<223> OTHER INFORMATION: n = any nucleotide
<220> FEATURE:
<221> NAME/KEY: misc_feature
<222> LOCATION: (645)..(645)
<223> OTHER INFORMATION: n = any nucleotide
<220> FEATURE:
<221> NAME/KEY: misc_feature
<222> LOCATION: (662)..(662)
<223> OTHER INFORMATION: n = any nucleotide
<220> FEATURE:
<221> NAME/KEY: misc_feature
<222> LOCATION: (669)..(669)
<223> OTHER INFORMATION: n = any nucleotide
<220> FEATURE:
<221> NAME/KEY: misc_feature
<222> LOCATION: (679)..(679)
<223> OTHER INFORMATION: n = any nucleotide
<220> FEATURE:
<221> NAME/KEY: misc_feature
<222> LOCATION: (682)..(682)
<223> OTHER INFORMATION: n = any nucleotide
<220> FEATURE:
<221> NAME/KEY: misc_feature
<222> LOCATION: (686)..(686)
<223> OTHER INFORMATION: n = any nucleotide
<220> FEATURE:
<221> NAME/KEY: misc_feature
<222> LOCATION: (693)..(693)
<223> OTHER INFORMATION: n = any nucleotide
<220> FEATURE:
<221> NAME/KEY: misc_feature
<222> LOCATION: (737)..(737)
<223> OTHER INFORMATION: n = any nucleotide
<220> FEATURE:
<221> NAME/KEY: misc_feature
<222> LOCATION: (762)..(762)
```

-continued

```
<223> OTHER INFORMATION: n = any nucleotide
<220> FEATURE:
<221> NAME/KEY: misc_feature
<222> LOCATION: (769)..(769)
<223> OTHER INFORMATION: n = any nucleotide

<400> SEQUENCE: 5

cagtgagccc aggagtcctc ggccagccct gcctgcccac caggaggatg aaggtctccg      60

tggctgccct ctcctgcctc atgcttgttg ctgtccttgg atcccaggcc cagttcataa     120

atgatgcaga gacagagtta atgatgtcaa agcttccact ggaaaatcca gtagttctga     180

acagctttca ctttgctgct gactgctgca cctcctacat ctcacaaagc atcccgtgtt     240

cactcatgaa aagttatttt gaaacgagca gcgagtgctc caagccaggt gtcatattcc     300

tcaccaagaa ggggnggcaa gtctgtgcca aacccagtgg tccgggagtt caggattgca     360

tgaaaaagct gaagccctac tcaatataat aataaagaga caaaagaggn cagccaccca     420

cctccaacac ctcctgtgag tttcttggtc tgaaatactt aaaaaatata tatattgttg     480

tgtctggtaa tgaaagtaat gcatctaata aagagtattc aattttttaa aaaaaaaaaa     540

aaaaaaaaaa aaaaaaaaaa aaaaaannct cggggggggg cccggtcccc aatccgccct     600

ntggggagtc gtttnaaaat ccactggccg ccgttttaaa acgtngggat tgggaaaacc     660

cnggggttnc ccaacttant cncctnggag aanatccccc tttccgccag ttggggttaa     720

tagggaagga ggcccgnacc gatccgccct tccccaaaag gnggggagn                 769


<210> SEQ ID NO 6
<211> LENGTH: 1071
<212> TYPE: DNA
<213> ORGANISM: Homo sapiens
<220> FEATURE:
<221> NAME/KEY: CDS
<222> LOCATION: (1)..(1071)
<223> OTHER INFORMATION:

<400> SEQUENCE: 6

atg aca acc tca cta gat aca gtt gag acc ttt ggt acc aca tcc tac       48
Met Thr Thr Ser Leu Asp Thr Val Glu Thr Phe Gly Thr Thr Ser Tyr
1               5                   10                  15

tat gat gac gtg ggc ctg ctc tgt gaa aaa gct gat acc aga gca ctg       96
Tyr Asp Asp Val Gly Leu Leu Cys Glu Lys Ala Asp Thr Arg Ala Leu
            20                  25                  30

atg gcc cag ttt gtg ccc ccg ctg tac tcc ctg gtg ttc act gtg ggc      144
Met Ala Gln Phe Val Pro Pro Leu Tyr Ser Leu Val Phe Thr Val Gly
        35                  40                  45

ctc ttg ggc aat gtg gtg gtg gtg atg atc ctc ata aaa tac agg agg      192
Leu Leu Gly Asn Val Val Val Val Met Ile Leu Ile Lys Tyr Arg Arg
    50                  55                  60

ctc cga att atg acc aac atc tac ctg ctc aac ctg gcc att tcg gac      240
Leu Arg Ile Met Thr Asn Ile Tyr Leu Leu Asn Leu Ala Ile Ser Asp
65                  70                  75                  80

ctg ctc ttc ctc gtc acc ctt cca ttc tgg atc cac tat gtc agg ggg      288
Leu Leu Phe Leu Val Thr Leu Pro Phe Trp Ile His Tyr Val Arg Gly
                85                  90                  95

cat aac tgg gtt ttt ggc cat ggc atg tgt aag ctc ctc tca ggg ttt      336
His Asn Trp Val Phe Gly His Gly Met Cys Lys Leu Leu Ser Gly Phe
            100                 105                 110

tat cac aca ggc ttg tac agc gag atc ttt ttc ata atc ctg ctg aca      384
Tyr His Thr Gly Leu Tyr Ser Glu Ile Phe Phe Ile Ile Leu Leu Thr
        115                 120                 125

atc gac agg tac ctg gcc att gtc cat gct gtg ttt gcc ctt cga gcc      432
```

-continued

```
Ile Asp Arg Tyr Leu Ala Ile Val His Ala Val Phe Ala Leu Arg Ala
    130                 135                 140

cgg act gtc act ttt ggt gtc atc acc agc atc gtc acc tgg ggc ctg      480
Arg Thr Val Thr Phe Gly Val Ile Thr Ser Ile Val Thr Trp Gly Leu
145                 150                 155                 160

gca gtg cta gca gct ctt cct gaa ttt atc ttc tat gag act gaa gag      528
Ala Val Leu Ala Ala Leu Pro Glu Phe Ile Phe Tyr Glu Thr Glu Glu
                165                 170                 175

ttg ttt gaa gag act ctt tgc agt gct ctt tac cca gag gat aca gta      576
Leu Phe Glu Glu Thr Leu Cys Ser Ala Leu Tyr Pro Glu Asp Thr Val
            180                 185                 190

tat agc tgg agg cat ttc cac act ctg aga atg acc atc ttc tgt ctc      624
Tyr Ser Trp Arg His Phe His Thr Leu Arg Met Thr Ile Phe Cys Leu
        195                 200                 205

gtt ctc cct ctg ctc gtt atg gcc atc tgc tac aca gga atc atc aaa      672
Val Leu Pro Leu Leu Val Met Ala Ile Cys Tyr Thr Gly Ile Ile Lys
    210                 215                 220

acg ctg ctg agg tgc ccc agt aaa aaa aag tac aag gcc atc cgg ctc      720
Thr Leu Leu Arg Cys Pro Ser Lys Lys Lys Tyr Lys Ala Ile Arg Leu
225                 230                 235                 240

att ttt gtc atc atg gcg gtg ttt ttc att ttc tgg aca ccc tac aat      768
Ile Phe Val Ile Met Ala Val Phe Phe Ile Phe Trp Thr Pro Tyr Asn
                245                 250                 255

gtg gct atc ctt ctc tct tcc tat caa tcc atc tta ttt gga aat gac      816
Val Ala Ile Leu Leu Ser Ser Tyr Gln Ser Ile Leu Phe Gly Asn Asp
            260                 265                 270

tgt gag cgg agc aag cat ctg gac ctg gac atg ctg gtg aca gag gtg      864
Cys Glu Arg Ser Lys His Leu Asp Leu Asp Met Leu Val Thr Glu Val
        275                 280                 285

atc gcc tac tcc cac tgg tgc tgc ctc aat ccc ctc atc tac gcc ttt      912
Ile Ala Tyr Ser His Trp Cys Cys Leu Asn Pro Leu Ile Tyr Ala Phe
    290                 295                 300

gtt gga gag agg ttc cgg aag tac ctg cgc cac ttc ttc cac agg cac      960
Val Gly Glu Arg Phe Arg Lys Tyr Leu Arg His Phe Phe His Arg His
305                 310                 315                 320

ttg ctc atg cac ctg ggc aga tac atc cca ttc ctt cct agt gag aag     1008
Leu Leu Met His Leu Gly Arg Tyr Ile Pro Phe Leu Pro Ser Glu Lys
                325                 330                 335

ctg gaa aga acc agc tct gtc tct cca tcc aca gga gag ccg gaa ctc     1056
Leu Glu Arg Thr Ser Ser Val Ser Pro Ser Thr Gly Glu Pro Glu Leu
            340                 345                 350

tct att gtg ttt tag                                                 1071
Ser Ile Val Phe
        355


<210> SEQ ID NO 7
<211> LENGTH: 356
<212> TYPE: PRT
<213> ORGANISM: Homo sapiens

<400> SEQUENCE: 7

Met Thr Thr Ser Leu Asp Thr Val Glu Thr Phe Gly Thr Thr Ser Tyr
1               5                   10                  15

Tyr Asp Asp Val Gly Leu Leu Cys Glu Lys Ala Asp Thr Arg Ala Leu
            20                  25                  30

Met Ala Gln Phe Val Pro Pro Leu Tyr Ser Leu Val Phe Thr Val Gly
        35                  40                  45

Leu Leu Gly Asn Val Val Val Val Met Ile Leu Ile Lys Tyr Arg Arg
    50                  55                  60
```

-continued

```
Leu Arg Ile Met Thr Asn Ile Tyr Leu Leu Asn Leu Ala Ile Ser Asp
65                  70                  75                  80

Leu Leu Phe Leu Val Thr Leu Pro Phe Trp Ile His Tyr Val Arg Gly
                85                  90                  95

His Asn Trp Val Phe Gly His Gly Met Cys Lys Leu Leu Ser Gly Phe
            100                 105                 110

Tyr His Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Leu Arg Ala
    130                 135                 140

Arg Thr Val Thr Phe Gly Val Ile Thr Ser Ile Val Thr Trp Gly Leu
145                 150                 155                 160

Ala Val Leu Ala Ala Leu Pro Glu Phe Ile Phe Tyr Glu Thr Glu Glu
                165                 170                 175

Leu Phe Glu Glu Thr Leu Cys Ser Ala Leu Tyr Pro Glu Asp Thr Val
            180                 185                 190

Tyr Ser Trp Arg His Phe His Thr Leu Arg Met Thr Ile Phe Cys Leu
        195                 200                 205

Val Leu Pro Leu Leu Val Met Ala Ile Cys Tyr Thr Gly Ile Ile Lys
    210                 215                 220

Thr Leu Leu Arg Cys Pro Ser Lys Lys Lys Tyr Lys Ala Ile Arg Leu
225                 230                 235                 240

Ile Phe Val Ile Met Ala Val Phe Phe Ile Phe Trp Thr Pro Tyr Asn
                245                 250                 255

Val Ala Ile Leu Leu Ser Ser Tyr Gln Ser Ile Leu Phe Gly Asn Asp
            260                 265                 270

Cys Glu Arg Ser Lys His Leu Asp Leu Asp Met Leu Val Thr Glu Val
        275                 280                 285

Ile Ala Tyr Ser His Trp Cys Cys Leu Asn Pro Leu Ile Tyr Ala Phe
    290                 295                 300

Val Gly Glu Arg Phe Arg Lys Tyr Leu Arg His Phe Phe His Arg His
305                 310                 315                 320

Leu Leu Met His Leu Gly Arg Tyr Ile Pro Phe Leu Pro Ser Glu Lys
                325                 330                 335

Leu Glu Arg Thr Ser Ser Val Ser Pro Ser Thr Gly Glu Pro Glu Leu
            340                 345                 350

Ser Ile Val Phe
        355
```

<210> SEQ ID NO 8
<211> LENGTH: 26
<212> TYPE: DNA
<213> ORGANISM: Artificial
<220> FEATURE:
<221> NAME/KEY: misc_feature
<222> LOCATION: (6)..(6)
<223> OTHER INFORMATION: n = deoxyinosine
<220> FEATURE:
<221> NAME/KEY: misc_feature
<222> LOCATION: (12)..(12)
<223> OTHER INFORMATION: n = deoxyinosine
<220> FEATURE:
<221> NAME/KEY: misc_feature
<222> LOCATION: (15)..(15)
<223> OTHER INFORMATION: n = deoxyinosine
<220> FEATURE:
<221> NAME/KEY: misc_feature
<222> LOCATION: (18)..(18)
<223> OTHER INFORMATION: n = deoxyinosine
<220> FEATURE:

-continued

```
<221> NAME/KEY: misc_feature
<222> LOCATION: (21)..(21)
<223> OTHER INFORMATION: n = deoxyinosine

<400> SEQUENCE: 8

gatcgntagc tngcnatngt ncaygc                                        26


<210> SEQ ID NO 9
<211> LENGTH: 26
<212> TYPE: DNA
<213> ORGANISM: Artificial
<220> FEATURE:
<221> NAME/KEY: misc_feature
<222> LOCATION: (6)..(6)
<223> OTHER INFORMATION: n = deoxyinosine
<220> FEATURE:
<221> NAME/KEY: misc_feature
<222> LOCATION: (7)..(7)
<223> OTHER INFORMATION: n = deoxyinosine
<220> FEATURE:
<221> NAME/KEY: misc_feature
<222> LOCATION: (8)..(8)
<223> OTHER INFORMATION: n = deoxyinosine
<220> FEATURE:
<221> NAME/KEY: misc_feature
<222> LOCATION: (12)..(12)
<223> OTHER INFORMATION: n = deoxyinosine
<220> FEATURE:
<221> NAME/KEY: misc_feature
<222> LOCATION: (15)..(15)
<223> OTHER INFORMATION: n = deoxyinosine
<220> FEATURE:
<221> NAME/KEY: misc_feature
<222> LOCATION: (21)..(21)
<223> OTHER INFORMATION: n = deoxyinosine

<400> SEQUENCE: 9

cggaannnmt cncsnacraa ngcrta                                        26
```

MAMMALIAN CHEMOKINE REAGENTS

This application is a divisional of co-pending application U.S. Ser. No. 08/567,882 now U.S. Pat. No. 6,512,103, filed on Dec. 8, 1995.

FIELD OF THE INVENTION

The present invention relates to compositions related to proteins which function in controlling development and differentiation of mammalian cells, e.g., cells of a mammalian immune system. In particular, it provides proteins and mimetics which regulate development, differentiation, and function of various cell types, including hematopoietic cells. It also provides receptor reagents for such proteins.

BACKGROUND OF THE INVENTION

The circulating component of the mammalian circulatory system comprises various cell types, including red and white blood cells of the erythroid or the myeloid cell lineages. See, e.g., Rapaport (1987) *Introduction to Hematology* (2d ed.) Lippincott, Philadelphia, Pa.; Jandl (1987) *Blood: Textbook of Hematology,* Little, Brown and Co., Boston, Mass.; and Paul (ed.)(1993) *Fundamental Immunology* 3d ed, Raven Press, N.Y. Progression through various stages of differentiation are regulated by various signals provided to the cells, often meidated through a class of proteins known as the cytokines. Within this group of molecules as a further group known as the chemoattractant cytokines, or chemokines. See, e.g., Schall (1994) "The Chemokines" in *The Cyokine Handbook* (2d ed.) Academic Press; Schall and Bacon (1994) *Current Opinion in Immunology* 6:865–873.

Although the full spectrum of biological activities of the chemokines has not been extensively investigated, chemoattractant effects are recognized. The best known biological functions of these molecules relate to chemoattraction of leukocytes. However, new chemokines are being discovered, and their biological effects on the various cells responsible for immunological responses are topics of continued study. Mouse CCF18 has been reported by a Japanese Group, and also published by the present inventors in Hara, et al. (1995) *J. Immunol.* 155:5352-5358.

These observations indicate that other factors exist whose functions in hematopoiesis, immune development, and leukocyte trafficking were heretofore unrecognized. These factors provide for biological activities whose spectra of effects are distinct from known differentiation, activation, or other signalling factors. The absence of knowledge about the structural, biological, and physiological properties of the regulatory factors which regulate hematopoietic cell physiology in vivo prevents the modification of the effects of such factors. Thus, medical conditions where regulation of the development or physiology of relevant cells is required remains unmanageable.

SUMMARY OF THE INVENTION

The present invention is based, in part, upon the discovery of new genes encoding CC chemokines, and new genes encoding various receptors for chemokines. It embraces agonists and antagonists of the chemokine designated CCF18, e.g., mutations (muteins) of the natural sequences, fusion proteins, chemical mimetics, antibodies, and other structural or functional analogues. It is also directed to isolated genes encoding proteins of the invention. Various uses of these different protein or nucleic acid compositions are also provided. Likewise for the receptor described herein.

The present invention provides a substantially pure CCF18 chemokine; a fusion protein comprising CCF18 chemokine sequence; an antibody specific for binding to a CCF18 chemokine; and a nucleic acid encoding a CCF18 chemokine or fusion protein thereof.

In CCF18 chemokine embodiments, the chemokine may be from a warm blooded animal selected from the group of birds and mammals, including a mouse or human; may comprise a sequence of Table 1 or 3; may exhibit a post-translational modification pattern distinct from natural CCF18 chemokine; or may exhibit the features disclosed in Table 2. The invention also embraces a composition comprising the chemokine and a pharmaceutically acceptable carrier.

In fusion protein embodiments, the protein may comprise either sequence of Table 1 or 3; and/or sequence of another cytokine or chemokine.

In antibody embodiments, the CCF18 chemokine can be a mammalian protein, including a mouse or human; or the antibody may be raised against a peptide sequence of Table 1 or 3; may be monoclonal antibody; or the antibody may be labeled.

In nucleic acid embodiments, the chemokine may be from a warm blooded animal selected from the group of birds and mammals, including a mouse or human. The nucleic acid may comprise a sequence of Table 1 or 3; be an expression vector; or comprise a deoxyribonucleic acid nucleotide.

The invention also provides a kit comprising a substantially pure CCF18 chemokine, or fragment thereof; an antibody which specifically binds a mammalian CCF18 chemokine; or a nucleic acid encoding a CCF18 chemokine or peptide. The kit may also be capable of making a qualitative or quantitative analysis.

In another embodiment, the invention provides methods of modulating physiology or development of a cell comprising contacting the cell with an agonist or antagonist of a mammalian CCF18 chemokine. The antagonist may be an antibody against a mammalian CCF18 chemokine. The cell may be a hematopoietic cell, including a lymphoid cell; a placenta cell; a gonad cell; or a neural cell, including neuronal or non-neuronal cells. Various of the physiological effects include effecting a cellular calcium flux; a chemoattractant response; cellular morphology modification responses; phosphoinositide lipid turnover; or an antiviral response.

The present invention also provides reagents related to a chemokine receptor, designated CCKR3. In particular embodiments, the invention provides a substantially pure CCKR3 chemokine receptor; a fusion protein comprising CCKR3 chemokine receptor sequence; an antibody specific for binding to a CCKR3 chemokine receptor; and a nucleic acid encoding a CCKR3 chemokine receptor or fusion protein thereof.

The CCKR3 may be from a warm blooded animal selected from the group of birds and mammals, including a mouse or human; may comprise a sequence of Table 4; or may exhibit a post-translational modification pattern distinct from natural CCKR3 chemokine receptor.

In receptor fusion embodiments, the protein may comprise sequence of Table 4; and/or sequence of another receptor for a chemokine.

In receptor antibody embodiments, the CCKR3 chemokine receptor may be a mammalian protein, including a mouse or human. The antibody may be raised against a peptide sequence of Table 4; may be a monoclonal antibody; or may be labeled.

In receptor nucleic acid embodiments, the chemokine receptor may be from a warm blooded animal selected from the group of birds and mammals, including a mouse or human. Alternatively, the nucleic acid may comprise a sequence of Table 4; may be an expression vector; or may comprise a deoxyribonucleic acid nucleotide.

DETAILED DESCRIPTION OF THE PREFERRED EMBODIMENTS

Outline

I. General

II. Purified Chemokine
- A. physical properties
- B. biological properties

III. Physical Variants
- A. sequence variants, fragments
- B. post-translational variants
- 1. glycosylation
- 2. others IV. Functional Variants
- A. analogs; fragments
- 1. agonists
- 2. antagonists
- B. mimetics
- 1. protein
- 2. chemicals
- C. species variants V. Antibodies
- A. polyclonal
- B. monoclonal
- C. fragments, binding compositions VI. Nucleic Acids
- A. natural isolates; methods
- B. synthetic genes
- C. methods to isolate VII. Making Chemokine; Mimetics
- A. recombinant methods
- B. synthetic methods
- C. natural purification VIII. Uses
- A. diagnostic
- B. therapeutic IX. Kits
- A. nucleic acid reagents
- B. protein reagents
- C. antibody reagents X. Receptor

I. General

The present invention provides DNA sequences encoding various mammalian proteins which exhibit structural properties characteristic of a chemotactic cytokine, or chemokine. See, e.g., Lodi, et al. (1994) *Science* 263:1762–1767; Gronenborn and Clore (1991) *Protein Engineering* 4:263–269; Miller and Kranger (1992) *Proc. Nat'l Acad. Sci. USA* 89:2950–2954; Matsushima and Oppenheim (1989) *Cytokine* 1:2–13; Stoeckle and Baker (1990) *New Biol.* 2:313–323; Oppenheim, et al. (1991) *Ann. Rev. Immunol.* 9:617–648; Schall (1991) *Cytokine* 3:165–183; and *The Cytokine Handbook* Academic Press, NY. Both mouse and human embodiments are described herein.

Chemokines play an important role in immune and inflammatory responses by inducing migration and adhesion of leukocytes. These small secreted molecules are a growing superfamily of 8–14 kDa proteins characterized by a conserved four cysteine motif. See, e.g., Schall (1991) *Cytokine* 3:165–183; and *The Cytokine Handbook* Academic Press, NY. Chemokines are secreted by activated leukocytes and act as a chemoattractant for a variety of cells which are involved in inflammation. Besides chemoattractant properties, chemokines have been shown to induce other biological responses, e.g., modulation of second messenger levels such as $Ca^{++}$; inositol phosphate pool changes (see, e.g., Berridge (1993) *Nature* 361:315–325 or Billah and Anthes (1990) *Biochem. J.* 269:281–291); cellular morphology modification responses; phosphoinositide lipid turnover; possible antiviral responses; and others. Thus, CCF18 may, alone or in combination with other therapeutic reagents, have advantageous combination effects. There are reasons to suggest that chemokines may have effects on other cell types, e.g., attraction or activation of monocytes, dendritic cells, T cells, eosinophils, and/or perhaps on basophils and/or neutrophils. They may also have chemoattractive effects on various neural cells including, e.g., doral root ganglia neurons in the peripheral nervous system and/or central nervous system neurons.

The chemokine superfamily is mainly divided into two main groups exhibiting characteristic structural motifs, the Cys-X-Cys (C—X—C) and Cys-Cys (C—C) families. These are distinguished on the basis of a single amino acid insertion between the NH-proximal pair of cysteine residues and sequence similarity. Typically, the C—X—C chemokines, i.e., IL-8 and MGSA/Gro-α act on neutrophils but not on monocytes, whereas the C—C chemokines, i.e., MIP-1α and RANTES, are potent chemoattractants for monocytes and lymphocytes but not neutrophils. See, e.g., Miller, et al. (1992) *Crit. Rev. Immunol.* 12:17–46. A recently isolated chemokine, lymphotactin, does not belong to either group and may constitute a first member of a third chemokine family, the C family. Lymphotactin does not have a characteristic CC or CXC motif, and acts on lymphocytes but not neutrophils and monocytes. See, e.g., Kelner et al. (1994) *Science* 266:1395–1399. The chemokine molecule described herein is a member of the C—C chemokine family and is designated CCF18.

In another embodiment, the invention provides a gene encoding a chemokine receptor designated CC chemokine receptor 3, or CCKR3. Its ligand has not yet specifically been identified. However, the receptor exhibits structural features typical of known chemokine receptors, e.g., it is a 7 transmembrane spanning structure. If may exhibit properties of binding many different cytokines at varying specificities (shared or promiscuous specificity) or may exhibit high affinity for one (specific) or a subset (shared) of the chemokines.

The described chemokine and receptor should be important for mediating various aspects of cellular physiology or development.

II. Purified CCF18 Chemokine

Mouse CCF18 chemokine nucleotide and amino acid sequences are shown in Table 1. Nucleotide and amino acid sequences of a human chemokine are provided in Table 3. The mouse and human nucleotide sequences correspond to SEQ ID NO: 1 and 3, respectively, and the mouse and human amino acid sequences correspond to SEQ ID NO: 2 and 4, respectively. The human chemokine exhibits similarity at the protein level of about 50% to the mouse counterpart. The nucleotide and amino acid sequences of the chemokine receptor, CCKR3, are provided in Table 4 and SEQ ID NO: 5 and 6. These amino acid sequences, provided amino to carboxy, are important in providing sequence information on the ligand allowing for distinguishing the protein from other proteins. Moreover, the peptide sequences allow preparation of peptides to generate antibodies to recognize such segments, and allow preparation of oligonucleotide probes, both of which are strategies for isolation, e.g., cloning, of genes encoding such sequences. Similarities have been observed with other cytokines. See, e.g., Bosenberg, et al. (1992) *Cell* 71:1157–1165; Huang, et. al. (1992) *Molecular Biology of the Cell* 3:349–362; and Pandiella, et al. (1992) *J. Biol. Chem.* 267:24028–24033. This will avoid certain problems of working with, or administering, a cell bound protein, and provides insight into possible mechanisms of cellular specificity.

TABLE 1

Nucleotide sequence (5' to 3') of CCF18 chemokine from mouse and the corresponding amino acid sequence (amino to carboxy), SEQ ID NO: 1 and 2. The conserved four cysteine residues and one potential RNA destabilizing sequence (ATTTA) are indicated by asterisks underneath. A predicted signal sequence, one potential N-glycosylation site (Asn-X-Ser/Thr), and two poly(A) addition signals (AATAAA) are underlined

| Sequence | |
|---|---|
| GCCTCGTGCC GAATTCGGCA CGAGGGGCCA GCTGGGTCTG CCCACTAAGA AG | 52 |
| ATG AAG CCT TTT CAT ACT GCC CTC TCC TTC CTC ATT CTT ACA ACT GCT | 100 |
| Met Lys Pro Phe His Thr Ala Leu Ser Phe Leu IleLeu Thr Thr Ala | 16 |
| CTT GGA ATC TGG GCC CAG ATC ACA CAT GCA ACA GAG ACA AAA GAA GTC | 148 |
| Leu Gly Ile Trp Ala Gln Ile Thr His Ala Thr Glu Thr Lys Glu Val | 32 |
| CAG AGC AGT CTG AAG GCA CAG CAA GGG CTT GAA ATT GAA ATG TTT CAC | 196 |
| Gln Ser Ser Leu Lys Ala Gln Gln Gly Leu Glu Ile Glu Met Phe His | 48 |
| ATG GGC TTT CAA GAC TCT TCA GAT TGC TGC CTG TCC TAT AAC TCA CGG | 244 |
| Met Gly Phe Gln Asp Ser Ser Asp Cys Cys Leu Ser Tyr Asn Ser Arg | 64 |
| * * | |
| ATT CAG TGT TCA AGA TTT ATA GGT TAT TTT CCC ACC AGT GGT GGG TGT | 292 |
| Ile Gln Cys Ser Arg Phe Ile Gly Tyr Phe Pro Thr Ser Gly Gly Cys | 80 |
| * | |
| ACC AGG CCG GGC ATC ATC TTT ATC AGC AAG AGG GGG TTC CAG GTC TGT | 340 |
| Thr Arg Pro Gly Ile Ile Phe Ile Ser Lys Arg Gly Phe Gln Val Cys | 96 |
| * | |
| GCC AAC CCC AGT GAT CGG AGA GTT CAG AGA TGC ATT GAA AGA TTG GAG | 388 |
| Ala Asn Pro Ser Asp Arg Arg Val Gln Arg Cys Ile Glu Arg Leu Glu | 112 |
| CAA AAC TCA CAA CCA CGG ACC TAC AAA CAA TAA CATTTGCTTG AAGAGAAGGG | 441 |
| Gln Asn Ser Gln Pro Arg Thr Tyr Lys Gln end | 122 |
| TGTGAACTGC CAGCTACTTT CTTTGGTCTT CCCCAGTGAC CACCTAAGCG GCTCTAAGTG | 501 |
| TTTATTTTTA TAGGTATATA AACATTTTTT TTTCTGTTCC ACTTTAAAGT GGCATATCTG | 561 |
| GCTTTGTCAC AGAGGGGAAA CTTGTCTGTG CCAACCCCAG TCATCTGAAA ACTCAGATGC | 621 |
| CTGCGGAAGG TCTGAAGCTG ACTCAATGAC TACACATAAT ATTTGATTGA GATAAATGGG | 681 |
| CAAGGTCTGG AGAGATGGCT TGGTGGTTAA GAGCACCTGC TGCTCTTCCA GAGGACCTGG | 741 |
| GTTCAATTCC CACTTAGATG GCAGCTCAAA CTATCTATAA TTCCAATTCC AAAGAAAACT | 801 |
| GATGCCCTAT TTTGCCCTTT AGTTAGTAGT ATTTACAGTA TTCTTTATAA ATTCACCTTG | 861 |
| **** | |
| ACATGACCAT CTTGAGCTAC AGCCATCCTA ACTGCCTCAG AATCACTCAA GTTCTTCCAC | 921 |
| TCGGTTTCCC AGCGGATTAT AAGTGGATAA ACTGTGAGAG TGGTCTGTGG GACTTTGGAA | 981 |
| TGTGTCTGGT TCTGATAGTC ACTTATGGCA ACCCGGGTAC ATTCAACTAG GATGAAATAA | 1041 |
| ATTCTGCCTT AGCCCAGTAG TATGTCTGTG TTTGTAAGGA CCCAGCTGAT TTTCCCACCA | 1101 |
| CCCCTCCATC AGTAAGCCAC TAATAAAGTG CATCTATGCA GCCAAAAAAA AAAAAAAAAA | 1161 |
| AAAA | 1065 |

TABLE 2

| Physical properties of mouse CCF18 chemokine. |
|---|
| open reading frame encoding a polypeptide of about 122 amino acids |
| mature protein of about 101 amino acids |
| 4 cysteine residues |
| molecular weight of about 11549 daltons |
| one potential N-glycosylation site |

TABLE 3

Human CC chemokine nucleic acid coding sequence. SEQ ID NO: 3 and 4.

| | | |
|---|---|---|
| 1 | ATGAAGGTCTCCGTGGCTGCCCTCTCCTGCCTCATGCTTGTTGCTGTCCTTGGATCCCAG | 60 |
| 1 | MetLysValSerValAlaAlaLeuSerCysLeuMetLeuValAlaValLeuGlySerGln | 20 |
| 61 | GCCCAGTTCATAAATGATGCAGAGACAGAGTTAATGATGTCAAAGCTTCCACTGGAAAAT | 120 |
| 21 | AlaGlnPheIleAsnAspAlaGluThrGluLeuMetMetSerLysLeuProLeuGluAsn | 40 |
| 121 | CCAGTAGTTCTGAACAGCTTTCACTTTGCTGCTGACTGCTGCACCTCCTACATCTCACAA | 180 |
| 41 | ProValValLeuAsnSerPheHisPheAlaAlaAspCysCysThrSerTyrIleSerGln | 60 |
| 181 | AGCATCCCGTGTTCACTCATGAAAAGTTATTTTGAAACGAGCAGCGAGTGCTCCAAGCCA | 240 |
| 61 | SerIleProCysSerLeuMetLysSerTyrPheGluThrSerSerGluCysSerLysPro | 80 |
| 241 | GGTGTCATATTCCTCACCAAGAAGGGGCGGCAAGTCTGTGCCAAACCCAGTGGTCCGGGA | 300 |
| 81 | GlyValIlePheLeuThrLysLysGlyArgGlnValCysAlaLysProSerGlyProGly | 100 |
| 301 | GTTCAGGATTGCATGAAAAAGCTGAAGCCCTACTCAATATAATAATAA | 348 |
| 101 | ValGlnAspCysMetLysLysLeuLysProTyrSerIleEndEndEnd | 116 |

Full length human CC chemokine

CAGTGAGCCCAGGAGTCCTCGGCCAGCCCTGCCTGCCCACCAGGAGG

ATGAAGGTCTCCGTGGCTGCCCTCTCCTGCCTCATGCTTGTTGCTGTCCTTGGATCCCAGGCCC

AGTTCATAAATGATGCAGAGACAGAGTTAATGATGTCAAAGCTTCCACTGGAAAATCCAGTAGT

TCTGAACAGCTTTCACTTTGCTGCTGACTGCTGCACCTCCTACATCTCACAAAGCATCCCGTGT

TCACTCATGAAAAGTTATTTTGAAACGAGCAGCGAGTGCTCCAAGCCAGGTGTCATATTCCTCA

CCAAGAAGGGGNGGCAAGTCTGTGCCAAACCCAGTGGTCCGGGAGTTCAGGATTGCATGAAAAA

GCTGAAGCCCTACTCAATATAATAATAAAGAGACAAAAGAGGNCAGCCACCCACCTCCAACACC

TCCTGTGAGTTTCTTGGTCTGAAATACTTAAAAAATATATATATTGTTGTGTCTGGTAATGAAA

GTAATGCATCTAATAAAGAGTATTCAATTTTTTAAAAAAAAAAAAAAAAAAAAAAAAAAAAAAA

AAAAAAANNCTCGGGGGGGGGCCCGGTCCCCAATCCGCCCTNTGGGGAGTCGTTTNAAAATCCA

CTGGCCGCCGTTTTAAAACGTNGGGATTGGGAAAACCCNGGGGTTNCCCAACTTANTCNCCTNG

GAGAANATCCCCCTTTCCGCCAGTTGGGGTTAATAGGGAAGGAGGCCCGNACCGATCCGCCCTT

CCCCAAAAGGNGGGGAGN

TABLE 4

Human chemokine receptor, CCKR3, nucleotide and amino acid sequences. SEQ ID NO: 5 and 6.

| | | |
|---|---|---|
| 1 | ATGACAACCTCACTAGATACAGTTGAGACCTTTGGTACCACATCCTACTATGATGACGTG | 60 |
| 1 | MetThrThrSerLeuAspThrValGluThrPheGlyThrThrSerTyrTyrAspAspVal | 20 |
| 61 | GGCCTGCTCTGTGAAAAAGCTGATACCAGAGCACTGATGGCCCAGTTTGTGCCCCCGCTG | 120 |
| 21 | GlyLeuLeuCysGluLysAlaAspThrArgAlaLeuMetAlaGlnPheValProProLeu | 40 |
| 121 | TACTCCCTGGTGTTCACTGTGGGCCTCTTGGGCAATGTGGTGGTGGTGATGATCCTCATA | 180 |
| 41 | TyrserLeuValpheThrValGlyLeuLeuGlyAsnValValValValMetIleLeuIle | 60 |

TABLE 4-continued

Human chemokine receptor, CCKR3, nucleotide and amino acid sequences. SEQ ID NO: 5 and 6.

```
 181 AAATACAGGAGGCTCCGAATTATGACCAACATCTACCTGCTCAACCTGGCCATTTCGGAC  240
  61 LysTyrArgArgLeuArgIleMetThrAsnIleTyrLeuLeuAsnLeuAlaIleSerAsp  80

 241 CTGCTCTTCCTCGTCACCCTTCCATTCTGGATCCACTATGTCAGGGGGCATAACTGGGTT  300
  81 LeuLeuPheLeuValThrLeuProPheTrpIleHisTyrValArgGlyHisAsnTrpVal  100

 301 TTTGGCCATGGCATGTGTAAGCTCCTCTCAGGGTTTTATCACACAGGCTTGTACAGCGAG  360
 101 PheGlyHisGlyMetCysLysLeuLeuSerGlyPheTyrHisThrGlyLeuTyrSerGlu  120

 361 ATCTTTTTCATAATCCTGCTGACAATCGACAGGTACCTGGCCATTGTCCATGCTGTGTTT  420
 121 IlePhePheIleIleLeuLeuThrIleAspArgTyrLeuAlaIleValHisAlaValPhe  100

 421 GCCCTTCGAGCCCGGACTGTCACTTTTGGTGTCATCACCAGCATCGTCACCTGGGGCCTG  480
 141 AlaLeuArgAlaArgThrValThrPheGlyValIleThrSerIleValThrTrpGlyLeu  160

 481 GCAGTGCTAGCAGCTCTTCCTGAATTTATCTTCTATGAGACTGAAGAGTTGTTTGAAGAG  540
 161 AlaValLeuAlaAlaLeuProGluPheIlePheTyrGluThrGluGluLeuPheGluGlu  180

 541 ACTCTTTGCAGTGCTCTTTACCCAGAGGATACAGTATATAGCTGGAGGCATTTCCACACT  600
 181 ThrLeuCysSerAlaLeuTyrProGluAspThrValTyrSerTrpArgHisPheHisThr  200

 601 CTGAGAATGACCATCTTCTGTCTCGTTCTCCCTCTGCTCGTTATGGCCATCTGCTACACA  660
 201 LeuArgMetThrIlePheCysLeuValLeuProLeuLeuValMetAlaIleCysTyrThr  220

 661 GGAATCATCAAAACGCTGCTGAGGTGCCCCAGTAAAAAAAAGTACAAGGCCATCCGGCTC  720
 221 GlyIleIleLysThrLeuLeuArgCysProSerLysLysLysTyrLysAlaIleArgLeu  240

 721 ATTTTTGTCATCATGGCGGTGTTTTTCATTTTCTGGACACCCTACAATGTGGCTATCCTT  780
 241 IlePheValIleMetAlaValPhePheIlePheTrpThrProTyrAsnValAlaIleLeu  260

 781 CTCTCTTCCTATCAATCCATCTTATTTGGAAATGACTGTGAGCGGAGCAAGCATCTGGAC  840
 261 LeuSerSerTyrGlnSerIleLeuPheGlyAsnAspCysGluArgSerLysHisLeuAsp  280

 841 CTGGACATGCTGGTGACAGAGGTGATCGCCTACTCCCACTGGTGCTGCCTCAATCCCCTC  900
 281 LeuAspMetLeuValThrGluValIleAlaTyrSerHisTrpCysCysLeuAsnProLeu  300

 901 ATCTACGCCTTTGTTGGAGAGAGGTTCCGGAAGTACCTGCGCCACTTCTTCCACAGGCAC  960
 301 IleTyrAlaPheValGlyGluArgPhearGLysTyrLeuArgHisPhePheHisArgHis  320

 961 TTGCTCATGCACCTGGGCAGATACATCCCATTCCTTCCTAGTGAGAAGCTGGAAAGAACC  1020
 321 LeuLeuMetHisLeuGlyArgTyrIleProPheLeuProSerGluLysLeuGluArgThr  340

1021 AGCTCTGTCTCTCCATCCACAGGAGAGCCGGAACTCTCTATTGTGTTTTAG          1072
 341 SerSerValSerProSerThrGlyGluProGluLeuSerIleValPheStop         358
```

As used herein, the term "CCF18 chemokine" shall encompass, when used in a protein context, a protein having mouse amino acid sequences shown in Table 1, or human amino acid sequences shown in Table 3. The invention also embraces a polypeptpide comprising a significant fragment of such proteins. It also refers to a mouse or human derived polypeptide which exhibits similar biological function or interacts with CCF18 chemokine specific binding components. These binding components, e.g., antibodies, typically bind to a CCF18 chemokine with high affinity, e.g., at least about 100 nM, usually better than about 30 nM, preferably better than about 10 nM, and more preferably at better than about 3 nM. Homologous proteins would be found in mammalian species other than mouse, e.g., rats. Non-mammalian species should also possess structurally or functionally related genes and proteins.

The term "polypeptide" as used herein includes a significant fragment or segment, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids, e.g., about 35, 40, 45, 50, 60, 75, 80, 100, 120, etc.

The term "binding composition" refers to molecules that bind with specificity to CCF18 chemokine, e.g., in a ligand-receptor type fashion or an antibody-antigen interaction. These compositions may be compounds, e.g., proteins, which specifically associate with CCF18 chemokine, including natural physiologically relevant protein-protein interactions, either covalent or non-covalent. The binding composition may be a polymer, or another chemical reagent. No implication as to whether the CCF18 chemokine presents a concave or convex shape in its ligand-receptor interaction is represented, other than the interaction exhibit similar specificity, e.g., specific affinity. A functional analog may be a ligand with structural modifications, or may be a wholly unrelated molecule, e.g., which has a molecular shape which interacts with the appropriate ligand binding determinants. The ligands may serve as agonists or antagonists of the receptor, see, e.g., Goodman, et al. (eds.) (1990) *Goodman & Gilman's: The Pharmacological Bases of Therapeutics* (8th ed.), Pergamon Press.

Substantially pure means that the protein is free from other contaminating proteins, nucleic acids, and other biologicals typically derived from the original source organism. Purity may be assayed by standard methods, and will ordinarily be at least about 40% pure, more ordinarily at least about 50% pure, generally at least about 60% pure, more generally at least about 70% pure, often at least about 75% pure, more often at least about 80% pure, typically at least about 85% pure, more typically at least about 90% pure, preferably at least about 95% pure, more preferably at least about 98% pure, and in most preferred embodiments, at least 99% pure.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The electrolytes will usually approximate in situ physiological conditions, but may be modified to higher or lower ionic strength where advantageous. The actual ions may be modified, e.g., to conform to standard buffers used in physiological or analytical contexts.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS or CHAPS, or a low enough concentration as to avoid significant disruption of structural or physiological properties of the ligand.

Solubility is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W. H. Freeman; and Cantor and Schimmel (1980) *Biophysical Chemistry,* parts 1–3, W. H. Freeman & Co., San Francisco. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S.

III. Physical Variants

This invention also encompasses proteins or peptides having substantial amino acid sequence homology with the amino acid sequence of the CCF18 chemokine. The variants include species or allelic variants.

Amino acid sequence homology, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are typically intended to include natural allelic and interspecies variations in each respective protein sequence. Typical homologous proteins or peptides will have from 25–100% homology (if gaps can be introduced), to 50–100% homology (if conservative substitutions are included) with the amino acid sequence of the CCF18 chemokine. Homology measures will be at least about 35%, generally at least 40%, more generally at least 45%, often at least 50%, more often at least 55%, typically at least 60%, more typically at least 65%, usually at least 70%, more usually at least 75%, preferably at least 80%, and more preferably at least 80%, and in particularly preferred embodiments, at least 85% or more. See also Needleham, et al. (1970) *J. Mol. Biol.* 48:443–453; Sankoff, et al. (1983) Chapter One in *Time Warps, String Edits, and Macromolecules: The Theory and Practice of Sequence Comparison* Addison-Wesley, Reading, Mass.; and software packages from IntelliGenetics, Mountain View, Calif.; and the University of Wisconsin Genetics Computer Group, Madison, Wis.

The isolated CCF18 chemokine DNA can be readily modified by nucleotide substitutions, nucleotide deletions, nucleotide insertions, and inversions of nucleotide stretches. These modifications result in novel DNA sequences which encode these antigens, their derivatives, or proteins having similar physiological, immunogenic, or antigenic activity. These modified sequences can be used to produce mutant antigens or to enhance expression. Enhanced expression may involve gene amplification, increased transcription, increased translation, and other mechanisms. Such mutant CCF18 chemokine derivatives include predetermined or site-specific mutations of the respective protein or its fragments. "Mutant CCF18 chemokine" encompasses a polypeptide otherwise falling within the homology definition of the mouse CCF18 chemokine as set forth above, but having an amino acid sequence which differs from that of CCF18 chemokine as found in nature, whether by way of deletion, substitution, or insertion. In particular, "site specific mutant CCF18 chemokine" generally includes proteins having significant homology with a ligand having sequences of Table 1 or 3, and as sharing various biological activities, e.g., antigenic or immunogenic, with those sequences, and in preferred embodiments contain most of the disclosed sequences. Similar concepts apply to different CCF18 chemokine proteins, particularly those found in various warm blooded animals, e.g., mammals and birds. As stated before, it is emphasized that descriptions are generally meant to encompass all CCF18 chemokine proteins, not limited to the mouse or human embodiments specifically discussed.

Although site specific mutation sites are predetermined, mutants need not be site specific. CCF18 chemokine mutagenesis can be conducted by making amino acid insertions or deletions. Substitutions, deletions, insertions, or any combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also Sambrook, et al. (1989) and Ausubel, et al. (1987 and Supplements).

The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with a CCF18 chemokine polypeptide is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional domains from other proteins. For example, ligand-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992. Thus, new chimeric polypeptides exhibiting new combinations of specificities will result from the functional linkage of ligand-binding specificities and other functional domains.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

IV. Functional Variants

The blocking of physiological response to CCF18 chemokines may result from the inhibition of binding of the ligand to its receptor, likely through competitive inhibition. Thus, in vitro assays of the present invention will often use isolated protein, membranes from cells expressing a recombinant membrane associated CCF18 chemokine, soluble fragments comprising receptor binding segments of these ligands, or fragments attached to solid phase substrates. These assays will also allow for the diagnostic determination of the effects of either binding segment mutations and modifications, or ligand mutations and modifications, e.g., ligand analogues.

This invention also contemplates the use of competitive drug screening assays, e.g., where neutralizing antibodies to antigen or receptor fragments compete with a test compound for binding to the protein. In this manner, the antibodies can be used to detect the presence of any polypeptide which shares one or more antigenic binding sites of the ligand and can also be used to occupy binding sites on the protein that might otherwise interact with a receptor.

Additionally, neutralizing antibodies against CCF18 chemokine and soluble fragments of the chemokine which contain a high affinity receptor binding site, can be used to inhibit chemokine activity in tissues, e.g., tissues experiencing abnormal physiology.

"Derivatives" of CCF18 chemokine antigens include amino acid sequence mutants, glycosylation variants, and covalent or aggregate conjugates with other chemical moieties. Covalent derivatives can be prepared by linkage of functionalities to groups which are found in CCF18 chemokine amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the CCF18 chemokine or fragments thereof with other proteins or polypeptides. These derivatives can be synthesized in recombinant culture such as N- or C-terminal fusions or by the use of agents known in the art for their usefulness in cross-linking proteins through reactive side groups. Preferred chemokine derivatization sites with cross-linking agents are at free amino groups, carbohydrate moieties, and cysteine residues.

Fusion polypeptides between CCF18 chemokines and other homologous or heterologous proteins, e.g., other chemokines, are also provided. Many growth factors and cytokines are homodimeric entities, and a repeat construct may have various advantages, including lessened susceptibility to proteolytic cleavage. Moreover, many receptors require dimerization to transduce a signal, and various dimeric ligands or domain repeats can be desirable. Homologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of a ligand, e.g., a receptor-binding segment, so that the presence or location of the fused ligand may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, a FLAG fusion, and yeast alpha mating factor. See, e.g., Godowski, et al. (1988) *Science* 241:812–816.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity tags as FLAG.

Fusion proteins will typically be made by either recombinant nucleic acid methods or by synthetic polypeptide methods. Techniques for nucleic acid manipulation and expression are described generally, for example, in Sambrook, et al. (1989) *Molecular Cloning: A Laboratory Manual* (2d ed.), Vols. 1–3, Cold Spring Harbor Laboratory. Techniques for synthesis of polypeptides are described, for example, in Merrifield (1963) *J. Amer. Chem. Soc.* 85:2149–2156; Merrifield (1986) *Science* 232: 341–347; and Atherton, et al. (1989) *Solid Phase Peptide Synthesis: A Practical Approach,* IRL Press, Oxford.

This invention also contemplates the use of derivatives of CCF18 chemokines other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of ligands or other binding ligands. For example, a CCF18 chemokine antigen can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-CCF18 chemokine antibodies or its receptor. The CCF18 chemokines can also be labeled with a detectable group, for example radioiodinated by the chloramine T procedure, covalently bound to rare earth chelates, or conjugated to another fluorescent moiety for use in diagnostic assays. Purification of CCF18 chemokine may be effected by immobilized antibodies or receptor.

A solubilized CCF18 chemokine or fragment of this invention can be used as an immunogen for the production of antisera or antibodies specific for the ligand or fragments thereof. The purified chemokines can be used to screen monoclonal antibodies or chemokine-binding fragments prepared by immunization with various forms of impure preparations containing the protein. In particular, the term "antibodies" also encompasses antigen binding fragments of natural antibodies. Purified CCF18 chemokine can also be used as a reagent to detect antibodies generated in response to the presence of elevated levels of the protein or cell fragments containing the protein, both of which may be diagnostic of an abnormal or specific physiological or disease condition. Additionally, chemokine protein fragments may also serve as immunogens to produce antibodies of the present invention, as described immediately below. For example, this invention contemplates antibodies raised against amino acid sequences shown in Tables 1 or 3, or proteins containing them. In particular, this invention contemplates antibodies having binding affinity to or being raised against specific fragments, e.g., those which are predicted to lie on the outside surfaces of protein tertiary structure.

The present invention contemplates the isolation of additional closely related species variants. Southern and Northern blot analysis should establish that similar genetic entities exist in other mammals. It is likely that CCF18 chemokines are widespread in species variants, e.g., rodents, lagomorphs, carnivores, artiodactyla, perissodactyla, and primates.

The invention also provides means to isolate a group of related chemokines displaying both distinctness and similarities in structure, expression, and function. Elucidation of many of the physiological effects of the proteins will be greatly accelerated by the isolation and characterization of distinct species variants of the ligands. In particular, the present invention provides useful probes for identifying additional homologous genetic entities in different species.

The isolated genes will allow transformation of cells lacking expression of a corresponding CCF18 chemokine, e.g., either species types or cells which lack corresponding ligands and exhibit negative background activity. Expression of transformed genes will allow isolation of antigenically pure cell lines, with defined or single specie variants. This approach will allow for more sensitive detection and discrimination of the physiological effects of CCF18 receptor proteins. Subcellular fragments, e.g., cytoplasts or membrane fragments, can be isolated and used.

Dissection of critical structural elements which effect the various differentiation functions provided by ligands is possible using standard techniques of modern molecular biology, particularly in comparing members of the related class. See, e.g., the homolog-scanning mutagenesis technique described in Cunningham, et al. (1989) *Science* 243: 1339–1336; and approaches used in O'Dowd, et al. (1988) *J. Biol. Chem.* 263:15985–15992; and Lechleiter, et al. (1990) *EMBO J.* 9:4381–4390.

In particular, receptor binding segments can be substituted between species variants to determine what structural features are important in both receptor binding affinity and specificity, as well as signal transduction. An array of different chemokine variants will be used to screen for ligands exhibiting combined properties of interaction with different receptor species variants.

Intracellular functions would probably involve segments of the receptor which are normally accessible to the cytosol. However, ligand internalization may occur under certain circumstances, and interaction between intracellular components and "extracellular" segments may occur. The specific segments of interaction of CCF18 chemokine with other intracellular components may be identified by mutagenesis or direct biochemical means, e.g., cross-linking or affinity methods. Structural analysis by crystallographic or other physical methods will also be applicable. Further investigation of the mechanism of signal transduction will include study of associated components which may be isolatable by affinity methods or by genetic means, e.g., complementation analysis of mutants.

Further study of the expression and control of CCF18 chemokine will be pursued. The controlling elements associated with the proteins may exhibit differential developmental, tissue specific, or other expression patterns. Upstream or downstream genetic regions, e.g., control elements, are of interest. Differential splicing of message may lead to membrane bound forms, soluble forms, and modified versions of ligand.

Structural studies of the proteins will lead to design of new ligands, particularly analogues exhibiting agonist or antagonist properties on the receptor. This can be combined with previously described screening methods to isolate ligands exhibiting desired spectra of activities.

Expression in other cell types will often result in glycosylation differences in a particular chemokine. Various species variants may exhibit distinct functions based upon structural differences other than amino acid sequence. Differential modifications may be responsible for differential function, and elucidation of the effects are now made possible.

Thus, the present invention provides important reagents related to a physiological chemokine-binding protein interaction. Although the foregoing description has focused primarily upon the mouse and human CCF18 chemokine, those of skill in the art will immediately recognize that the invention encompasses other species counterparts, e.g., rat and other mammalian species or allelic variants, as well as variants thereof.

V. Antibodies

Antibodies can be raised to CCF18 chemokines, including species or allelic variants, and fragments thereof, both in their naturally occurring forms and in their recombinant forms. Additionally, antibodies can be raised to CCF18 chemokines in either their active forms or in their inactive forms. Anti-idiotypic antibodies are also contemplated.

Antibodies, including binding fragments and single chain versions, against predetermined fragments of the ligands can be raised by immunization of animals with conjugates of the fragments with immunogenic proteins. Monoclonal antibodies are prepared from cells secreting the desired antibody. These antibodies can be screened for binding to normal or defective CCF18 chemokines, or screened for agonistic or antagonistic activity, e.g., mediated through a receptor for CCF18. These monoclonal antibodies will usually bind with at least a $K_D$ of about 1 mM, more usually at least about 300 μM, typically at least about 10 μM, more typically at least about 30 μM, preferably at least about 10 μM, and more preferably at least about 3 μM or better.

The antibodies, including antigen binding fragments, of this invention can have significant diagnostic or therapeutic value. They can be potent antagonists that bind to a receptor and inhibit ligand binding or inhibit the ability of a ligand to elicit a biological response. They also can be useful as non-neutralizing antibodies and can be coupled to toxins or radionuclides so that when the antibody binds to ligand, a cell expressing it, e.g., on its surface, is killed. Further, these antibodies can be conjugated to drugs or other therapeutic agents, either directly or indirectly by means of a linker, and may effect drug targeting.

The antibodies of this invention can also be useful in diagnostic applications. As capture or non-neutralizing antibodies, they can be screened for ability to bind to the chemokines without inhibiting receptor binding. As neutralizing antibodies, they can be useful in competitive binding assays. They will also be useful in detecting or quantifying CCF18 chemokine or, indirectly, receptors.

Ligand fragments may be joined to other materials, particularly polypeptides, as fused or covalently joined polypeptides to be used as immunogens. A ligand and its fragments may be fused or covalently linked to a variety of immunogens, such as keyhole limpet hemocyanin, bovine serum albumin, tetanus toxoid, etc. See *Microbiology,* Hoeber Medical Division, Harper and Row, 1969; Landsteiner (1962) *Specificity of Serological Reactions,* Dover Publications, New York, and Williams, et al. (1967) *Methods in Immunology and Immunochemistry,* Vol. 1, Academic Press, New York, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual,* CSH Press; Goding (1986) *Monoclonal Antibodies: Principles and Practice* (2d ed.) Academic Press, New York; and particularly in Kohler and Milstein (1975) in *Nature* 256:495–497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or “hybridoma” that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse, et al. (1989) “Generation of a Large Combinatorial Library of the Immunoglobulin Repertoire in Phage Lambda,” *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567; and Queen et al. (1989) *Proc. Nat'l. Acad. Sci.* 86:10029–10033.

The antibodies of this invention can also be used for affinity chromatography in isolating the protein. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified CCF18 chemokine protein will be released.

The antibodies may also be used to screen expression libraries for particular expression products. Usually the antibodies used in such a procedure will be labeled with a moiety allowing easy detection of presence of antigen by antibody binding.

Antibodies raised against CCF18 chemokine will also be useful to raise anti-idiotypic antibodies. These will be useful in detecting or diagnosing various immunological conditions related to expression of the respective antigens.

VI. Nucleic Acids

The described peptide sequences and the related reagents are useful in isolating a DNA clone encoding CCF18 chemokine, e.g., from a natural source. Typically, it will be useful in isolating a gene from mouse, and similar procedures will be applied to isolate genes from other species, e.g., warm blooded animals, such as birds and mammals. Cross hybridization will allow isolation of ligand from other species. A number of different approaches should be available to successfully isolate a suitable nucleic acid clone.

The purified protein or defined peptides are useful for generating antibodies by standard methods, as described above. Synthetic peptides or purified protein can be presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. Alternatively, a CCF18 receptor can be used as a specific binding reagent, and advantage can be taken of its specificity of binding, much like an antibody would be used. However, chemokine receptors are typically 7 transmembrane proteins, which could be senstive to appropriate interaction with lipid or membrane.

For example, the specific binding composition could be used for screening of an expression library made from a cell line which expresses a CCF18 chemokine. The screening can be standard staining of surface expressed ligand, or by panning. Screening of intracellular expression can also be performed by various staining or immunofluorescence procedures. The binding compositions could be used to affinity purify or sort out cells expressing the ligand.

The peptide segments can also be used to predict appropriate oligonucleotides to screen a library, e.g., to isolate species variants. The genetic code can be used to select appropriate oligonucleotides useful as probes for screening. See, e.g., Table 1 or 3. In combination with polymerase chain reaction (PCR) techniques, synthetic oligonucleotides will be useful in selecting correct clones from a library. Complementary sequences will also be used as probes or primers. Based upon identification of the likely amino terminus, the third peptide should be particularly useful, e.g., coupled with anchored vector or poly-A complementary PCR techniques or with complementary DNA of other peptides.

This invention contemplates use of isolated DNA or fragments to encode a biologically active corresponding CCF18 chemokine polypeptide. In addition, this invention covers isolated or recombinant DNA which encodes a biologically active protein or polypeptide which is capable of hybridizing under appropriate conditions with the DNA sequences described herein. Said biologically active protein or polypeptide can be an intact ligand, or fragment, and have an amino acid sequence as disclosed in Table 1 or 3. Further, this invention covers the use of isolated or recombinant DNA, or fragments thereof, which encode proteins which are homologous to a CCF18 chemokine or which was isolated using cDNA encoding a CCF18 chemokine as a probe. The isolated DNA can have the respective regulatory sequences in the 5' and 3' flanks, e.g., promoters, enhancers, poly-A addition signals, and others.

An "isolated" nucleic acid is a nucleic acid, e.g., an RNA, DNA, or a mixed polymer, which is substantially separated from other components which naturally accompany a native sequence, e.g., ribosomes, polymerases, and flanking genomic sequences from the originating species. The term embraces a nucleic acid sequence which has been removed from its naturally occurring environment, and includes recombinant or cloned DNA isolates and chemically synthesized analogs or analogues biologically synthesized by heterologous systems. A substantially pure molecule includes isolated forms of the molecule.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

A significant "fragment" in a nucleic acid context is a contiguous segment of at least about 17 nucleotides, generally at least about 20 nucleotides, more generally at least about 23 nucleotides, ordinarily at least about 26 nucleotides, more ordinarily at least about 29 nucleotides, often at least about 32 nucleotides, more often at least about 35 nucleotides, typically at least about 38 nucleotides, more typically at least about 41 nucleotides, usually at least about 44 nucleotides, more usually at least about 47 nucleotides, preferably at least about 50 nucleotides, more preferably at least about 53 nucleotides, and in particularly preferred embodiments will be at least about 56 or more nucleotides, e.g., 60, 65, 75, 85, 100, 120, 150, 200, 250, 300, 400, etc.

A DNA which codes for a CCF18 chemokine protein or peptide will be particularly useful to identify genes, mRNA, and cDNA species which code for related or homologous ligands, as well as DNAs which code for homologous proteins from different species. There are likely homologues in other species, including primates. Various CCF18 chemokine proteins should be homologous and are encompassed herein. However, even proteins that have a more distant evolutionary relationship to the ligand can readily be isolated under appropriate conditions using these sequences if they are sufficiently homologous. Primate CCF18 chemokines are of particular interest.

This invention further covers recombinant DNA molecules and fragments having a DNA sequence identical to or highly homologous to the isolated DNAs set forth herein. In particular, the sequences will often be operably linked to DNA segments which control transcription, translation, and DNA replication. Alternatively, recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology* Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987)(ed.) *Teratocarcinomas and Embryonic Stem Cells: A Practical Approach* IRL Press, Oxford; and Rosenberg (1992) *J. Clinical Oncology* 10:180–199.

Homologous nucleic acid sequences, when compared, exhibit significant similarity. The standards for homology in nucleic acids are either measures for homology generally used in the art by sequence comparison or based upon hybridization conditions. The hybridization conditions are described in greater detail below.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least about 56%, more generally at least about 59%, ordinarily at least about 62%, more ordinarily at least about 65%, often at least about 68%, more often at least about 71%, typically at least about 74%, more typically at least about 77%, usually at least about 80%, more usually at least about 85%, preferably at least about 90%, more preferably at least about 95 to 98% or more, and in particular embodiments, as high at about 99% or more of the nucleotides. Alternatively, substantial homology exists when the segments will hybridize under selective hybridization conditions, to a strand, or its complement, typically using a sequence derived from Table 1 or 3. Typically, selective hybridization will occur when there is at least about 55% homology over a stretch of at least about 30 nucleotides, preferably at least about 65% over a stretch of at least about 25 nucleotides, more preferably at least about 75%, and most preferably at least about 90% over about 20 nucleotides. See, Kanehisa (1984) *Nuc. Acids Res.* 12:203–213. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is much more important than the measure of any single parameter. See, e.g., Wetmur and Davidson (1968) *J. Mol. Biol.* 31:349–370.

CCF18 chemokine from other mammalian species can be cloned and isolated by cross-species hybridization of closely related species. Alternatively, sequences from a data base may be recognized as having similarity. Homology may be relatively low between distantly related species, and thus hybridization of relatively closely related species is advisable. Alternatively, preparation of an antibody preparation which exhibits less species specificity may be useful in expression cloning approaches.

VII. Making CCF18 Chemokine; Mimetics

DNA which encodes the CCF18 chemokine or fragments thereof can be obtained by chemical synthesis, screening cDNA libraries, or by screening genomic libraries prepared from a wide variety of cell lines or tissue samples.

This DNA can be expressed in a wide variety of host cells for the synthesis of a full-length ligand or fragments which can in turn, for example, be used to generate polyclonal or monoclonal antibodies; for binding studies; for construction and expression of modified molecules; and for structure/function studies. Each antigen or its fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, or portions thereof, may be expressed as fusions with other proteins.

Expression vectors are typically self-replicating DNA or RNA constructs containing the desired antigen gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention contain DNA which encodes a CCF18 chemokine, or a fragment thereof, typically encoding a biologically active polypeptide. The DNA can be under the control of a viral promoter and can encode a selection marker. This invention further contemplates use of such expression vectors which are capable of expressing eukaryotic cDNA coding for a CCF18 chemokine in a prokaryotic or eukaryotic host, where the vector is compatible with the host and where the eukaryotic cDNA coding for the ligand is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the ligand or its fragments in various hosts using vectors that do not contain a replication origin that is recognized by the host cell. It is also possible to use vectors that cause integration of a CCF18 chemokine gene or its fragments into the host DNA by recombination, or to integrate a promoter which controls expression of an endogenous gene.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels, et al. (1985 and Supplements) *Cloning Vectors: A Laboratory Manual,* Elsevier, N.Y., and Rodriquez, et al. (1988)(eds.) *Vectors: A Survey of Molecular Cloning Vectors and Their Uses,* Buttersworth, Boston, Mass.

Transformed cells include cells, preferably mammalian, that have been transformed or transfected with CCF18 chemokine gene containing vectors constructed using recombinant DNA techniques. Transformed host cells usually express the ligand or its fragments, but for purposes of cloning, amplifying, and manipulating its DNA, do not need to express the protein. This invention further contemplates culturing transformed cells in a nutrient medium, thus permitting the protein to accumulate in the culture. The protein can be recovered, either from the culture or from the culture medium.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and *Pichia*, and species of the genus *Dictyostelium*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the CCF18 chemokines or its fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses,* Buttersworth, Boston, Chapter 10, pp. 205–236.

Lower eukaryotes, e.g., yeasts and *Dictyostelium*, may be transformed with CCF18 chemokine sequence containing vectors. For purposes of this invention, the most common lower eukaryotic host is the baker's yeast, *Saccharomyces cerevisiae*. It will be used to generically represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are the preferred host cells for expression of the functionally active CCF18 chemokine protein. In principle, any higher eukaryotic tissue culture cell line is workable, e.g., insect baculovirus expression systems, whether from an invertebrate or vertebrate source. However, mammalian cells are preferred, in that the processing, both cotranslationally and posttranslationally. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pcDNA1; pCD, see Okayama, et al. (1985) *Mol. Cell Biol.* 5:1136–1142; pMClneo Poly-A, see Thomas, et al. (1987) *Cell* 51:503–512; and a baculovirus vector such as pAC 373 or pAC 610.

It will often be desired to express a CCF18 chemokine polypeptide in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the CCF18 chemokine gene may be co-transformed with one or more genes encoding mammalian or other glycosylating enzymes. Using this approach, certain mammalian glycosylation patterns will be achievable or approximated in prokaryote or other cells.

A CCF18 chemokine, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427–454; Tse, et al. (1985) *Science* 230:1003–1008; and Brunner, et al. (1991) *J. Cell Biol.* 114:1275–1283.

Now that the CCF18 chemokine has been characterized, fragments or derivatives thereof can be prepared by conventional processes for synthesizing peptides. These include processes such as are described in Stewart and Young (1984) *Solid Phase Peptide Synthesis,* Pierce Chemical Co., Rockford, Ill.; Bodanszky and Bodanszky (1984) *The Practice of Peptide Synthesis,* Springer-Verlag, New York; and Bodanszky (1984) *The Principles of Peptide Synthesis,* Springer-Verlag, New York. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The CCF18 chemokine, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction are typically protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonyl-hydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield, et al. (1963) in *J. Am. Chem. Soc.* 85:2149–2156.

The prepared ligand and fragments thereof can be isolated and purified from the reaction mixture by means of peptide separation, e.g., by extraction, precipitation, electrophoresis and various forms of chromatography, and the like. The CCF18 chemokines of this invention can be obtained in varying degrees of purity depending upon its desired use. Purification can be accomplished by use of the protein purification techniques disclosed herein or by the use of the antibodies herein described in immunoabsorbant affinity chromatography. This immunoabsorbant affinity chromatography is carried out by first linking the antibodies to a solid support and then contacting the linked antibodies with solubilized lysates of appropriate source cells, lysates of other cells expressing the ligand, or lysates or supernatants of cells producing the CCF18 chemokine as a result of DNA techniques, see below.

VIII. Uses

The present invention provides reagents which will find use in diagnostic applications as described elsewhere herein, e.g., in the general description for developmental abnormalities, or below in the description of kits for diagnosis.

This invention also provides reagents with significant therapeutic value. The CCF18 chemokine (naturally occurring or recombinant), fragments thereof and antibodies thereto, along with compounds identified as having binding affinity to CCF18 chemokine, should be useful in the treatment of conditions associated with abnormal physiology or development, including inflammatory conditions. In particular, modulation of trafficking of leukocytes is likely, but a wider tissue distribution might suggest broader biological activity, including, e.g., antiviral effects. Abnormal proliferation, regeneration, degeneration, and atrophy may be modulated by appropriate therapeutic treatment using the compositions provided herein. For example, a disease or disorder associated with abnormal expression or abnormal signaling by a CCF18 chemokine should be a likely target for an agonist or antagonist of the ligand.

Various abnormal physiological or developmental conditions are known in cell types shown to possess CCF18 mRNA by Northern blot analysis. See Berkow (ed.) *The Merck Manual of Diagnosis and Therapy,* Merck & Co., Rahway, N.J.; and Thorn, et al. *Harrison's Principles of Internal Medicine,* McGraw-Hill, N.Y. Developmental or functional abnormalities, e.g., of the immune system, cause significant medical abnormalities and conditions which may be susceptible to prevention or treatment using compositions provided herein.

Recombinant CCF18 chemokine antibodies can be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using antibodies or receptor or fragments thereof can be performed to identify compounds having binding affinity to CCF18 chemokine, including isolation of associated components. Subsequent biological assays can then be utilized to determine if the compound has intrinsic stimulating activity and is therefore a blocker or antagonist in that it blocks the activity of the ligand. Likewise, a compound having intrinsic stimulating activity can activate the receptor and is thus an agonist in that it simulates the activity of CCF18 chemokine. This invention further contemplates the therapeutic use of antibodies to CCF18 chemokine as antagonists. This approach should be particularly useful with other CCF18 chemokine species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 μM concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

CCF18 chemokine, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacoloaical Bases of Therapeutics,* 8th Ed., Pergamon Press; and *Remi-naton's Pharmaceutical Sciences,* 17th ed. (1990), Mack Publishing Co., Easton, Pennsylvana; Avis, et al. (eds.) (1993) *Pharmaceutical Dosage Forms: Parenteral Medications* Dekker, New York; Lieberman, et al. (eds.) (1990) *Pharmaceutical Dosage Forms: Tablets* Dekker, New York; and Lieberman, et al. (eds.) (1990) *Pharmaceutical Dosage Forms: Disperse Systems* Dekker, New York. The therapy of this invention may be combined with or used in association with other chemotherapeutic or chemopreventive agents.

Both the naturally occurring and the recombinant form of the CCF18 chemokines of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, which describes means for testing of binding affinity by a plurality of defined polymers synthesized on a solid substrate. The development of suitable assays can be greatly facilitated by the availability of large amounts of purified, soluble CCF18 chemokine as provided by this invention.

For example, antagonists can normally be found once the ligand has been structurally defined. Testing of potential ligand analogs is now possible upon the development of highly automated assay methods using physiologially responsive cells. In particular, new agonists and antagonists will be discovered by using screening techniques described herein.

Viable cells could also be used to screen for the effects of drugs on CCF18 chemokine mediated functions, e.g., second messenger levels, i.e., $Ca^{++}$; inositol phosphate pool changes (see, e.g., Berridge (1993) *Nature* 361:315–325 or Billah and Anthes (1990) *Biochem. J.* 269:281–291); cellular morphology modification responses; phosphoinositide lipid turnover; an antiviral response, and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus.

Rational drug design may also be based upon structural studies of the molecular shapes of the CCF18 chemokine and other effectors or analogues. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography,* Academic Press, New York.

Purified CCF18 chemokine can be coated directly onto plates for use in the aforementioned drug screening techniques. However, non-neutralizing antibodies to these ligands can be used as capture antibodies to immobilize the respective ligand on the solid phase.

IX. Kits

This invention also contemplates use of CCF18 chemokine proteins, fragments thereof, peptides, and their fusion products in a variety of diagnostic kits and methods for detecting the presence of ligand, antibodies, or a CCF18 chemokine receptor. Typically the kit will have a compartment containing either a defined CCF18 chemokine peptide or gene segment or a reagent which recognizes one or the other, e.g., antibodies.

A kit for determining the binding affinity of a test compound to a CCF18 chemokine would typically comprise a test compound; a labeled compound, for example an antibody having known binding affinity for the ligand; a source of CCF18 chemokine (naturally occurring or recombinant); and a means for separating bound from free labeled compound, such as a solid phase for immobilizing the ligand. Once compounds are screened, those having suitable binding affinity to the ligand can be evaluated in suitable biological assays, as are well known in the art, to determine whether they act as agonists or antagonists to the receptor. The availability of recombinant CCF18 chemokine polypeptides also provide well defined standards for calibrating such assays.

A preferred kit for determining the concentration of, for example, a CCF18 chemokine in a sample would typically comprise a labeled compound, e.g., antibody, having known binding affinity for the ligand, a source of ligand (naturally occurring or recombinant) and a means for separating the bound from free labeled compound, for example, a solid phase for immobilizing the CCF18 chemokine. Compartments containing reagents, and instructions, will normally be provided.

Antibodies, including antigen binding fragments, specific for the CCF18 chemokine or ligand fragments are useful in diagnostic applications to detect the presence of elevated levels of CCF18 chemokine and/or its fragments. Such diagnostic assays can employ lysates, live cells, fixed cells, immunofluorescence, cell cultures, body fluids, and further can involve the detection of antigens related to the ligand in serum, or the like. Diagnostic assays may be homogeneous (without a separation step between free reagent and antigen-ligand complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to a CCF18 chemokine or to a particular fragment thereof. Similar assays have also been extensively discussed in the literature. See, e.g., Harlow and Lane (1988) *Antibodies: A Laboratory Manual,* CSH.

Anti-idiotypic antibodies may have similar use to diagnose presence of antibodies against a CCF18 chemokine, as such may be diagnostic of various abnormal states. For example, overproduction of CCF18 chemokine may result in production of various immunological reactions which may be diagnostic of abnormal physiological states, particularly in various inflammatory conditions.

Frequently, the reagents for diagnostic assays are supplied in kits, so as to optimize the sensitivity of the assay. For the subject invention, depending upon the nature of the assay, the protocol, and the label, either labeled or unlabeled antibody or labeled CCF18 chemokine is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Any of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the ligand, test compound, CCF18 chemokine, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free ligand, or alternatively the bound from the free test compound. The CCF18 chemokine can be immobilized on various matrixes followed by washing. Suitable matrixes include plastic such as an ELISA plate, filters, and beads. Methods of immobilizing the CCF18 chemokine to a matrix include, without limitation, direct adhesion to plastic, use of a capture antibody, chemical coupling, and biotin-avidin. The last step in this approach involves the precipitation of ligand/antibody complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a CCF18 chemokine. These sequences can be used as probes for detecting levels of the ligand message in samples from patients suspected of having an abnormal condition, e.g., an inflammatory or developmental problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

X. Receptor

Having isolated a ligand binding partner of a specific interaction, methods exist for islating the counter-partner. See, Gearing, et al *EMBO. J.* 8:3667–4676. For example, means to label a CCF18 chemokine without interfering with the binding to its receptor can be determined. For example, an affinity label can be fused to either the amino- or carboxy-terminus of the ligand. An expression library can be screened for specific binding of the CCF18 chemokine, e.g., by cell sorting, or other screening to detect subpopulations which express such a binding component. See, e.g., Ho, et al. (1993) *Proc. Nat'l Acad, Sci.* 90:11267–11271. Alternatively, a panning method may be used. See, e.g., Seed and Aruffo (1987) *Proc. Nat'l. Acad. Sci.* 84:3365–3369.

Protein cross-linking techniques with label can be applied to a isolate binding partners of a CCF18 chemokine. This would allow identification of protein which specifically interacts with a CCF18 chemokine, e.g., in a ligand-receptor like manner.

In another embodiment, a new receptor designated CC CKR3 was isolated. The sequences of the human construct and product are provided in Table 4. Similar means for making variants, at the nucleotide level or at the protein level, and making antibodies will be available as described above. Many similar or related uses to the ligands will be applied to the receptors, as specific binding reagents. Many uses, including kits, will also be available through analogous techniques.

The broad scope of this invention is best understood with reference to the following examples, which are not intended to limit the invention to specific embodiments.

EXAMPLES

I. General Methods

Some of the standard methods are described or referenced, e.g., in Maniatis, et al. (1982) *Molecular Cloning, A Laboratory Manual,* Cold Spring Harbor Laboratory, Cold Spring Harbor Press; Sambrook, et al. (1989) *Molecular Cloning: A Laboratory Manual,* (2d ed.), vols 1–3, CSH Press, NY; Ausubel, et al., *Biology*, Greene Publishing Associates, Brooklyn, N.Y.; or Ausubel, et al. (1987 and Supplements) *Current Protocols in Molecular Biology,* Greene/Wiley, New York; Innis, et al. (eds.)(1990) *PCR Protocols: A Guide to Methods and Applications* Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology,* vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *QIAexpress: The High Level Expression & Protein Purification System* QUIAGEN, Inc., Chatsworth, Calif.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Isolation and Sequencing of Mouse and Human CCF18 cDNA

BF-EGFR/EPORH is a Ba/F3 (mouse pre-B cell line; see Palacios, et al. (1985) *Cell* 41:727–734; and Palacios, et al. (1984) *Nature* 309:126–131) transfectant expressing a chimeric receptor between the extracellular domain of the epidermal growth factor (EGF) receptor and the cytoplasmic domain of the erythropoietin receptor and proliferates in response to either IL-3 or EGF, see, e.g., Maruyama, et al. (1994) *J. Biol. Chem.* 269:5976–5980. BF-EGFR/EPORH cells were maintained in RPMI 1640 containing 10% fetal calf serum (FCS) and IL-3 (100 units/ml). COS cells were cultured in DMEM containing 10% FCS. A cDNA library was made from EGF-stimulated BF-EGFR/EPORH cells, see, e.g., Yoshimura, et al. (1995) *EMBO J.* 14:2816–2826. Isolation of poly(A)+ RNA, cDNA synthesis, and ligation into the expression vector, pME18S, were carried out as described Hara, et al. (1994) *Blood* 84:189–199.

The sequence of the CCF18 cDNA insert was determined by the Taq DyeDeoxy Terminator Cycle Sequencing kit (Applied Biosystems, Foster City, Calif.) using oligonucleotide primers corresponding to the sequences of the vector and the cDNA insert. The open reading fram of mouse CCF18 cDNA encodes a polypeptide of 123 amino acids including a putative signal sequence of 21 amino acid residues. The mature protein consists of about 102 amino acids with a calculated molecular weight of 11548 daltons. Computer searches with other C—C chemokine family members revealed significant homology at the amino acid levels with MIP-1β (67%), MIP-1 (56%), JE (55%), RANTES (48%), lymphotactin (48%), and NSGA/Gro-α (43%).

A human fetal spleen cDNA library was purchased from Stratagene, though other libraries might also be successfully used. The library was screened by standard methods using mouse CCF18 as a probe. See Hara, et al. (1995) *J. Immunol.* 155:5352–5358. The isolate is described above and in Table 3.

III. Chromosomal Location of Mouse CCF18

Interspecific backcross progeny were generated by mating (C57BL/6J×*M. spretus*) F1 females and C57BL/6J males as described in Copeland, et al. (1991) *Trends Genet.* 7:113–118. A total of 205 backcross mice were used to map the CCF18 gene, the Scya10 locus. DNA isolation, restriction enzyme digestion, agarose gel electrophoresis, Southern blot transfer, and hybridization were performed essentially as described in Jenkins, et al. (1982) *J. Virol.* 43:26–36. All blots were prepared with Hybond-N+ nylon membrane (Amersham). The Scya10 probe, an ~1.1 kb EcoRI/NotI fragment of the CCF18 cDNA, was labeled with [$\alpha$-$^{32}$P] dCTP using a nick translation labeling kit (Boehringer Mannheim); washing was done to a final stringency of 0.1×SSCP, 0.1% SDS, 65° C. A 7.8 kb fragment was detected in BamHI-digested C57BL/6J DNA, while a 5.1 kb fragment was detected in *M. spretus* DNA. The presence or absence of the 5.1 kb *M. spretus*-specific BamHI fragment was followed in backcross mice.

A description of the probes and RFLPs for two of the loci linked to Scya10 including neurofibromatosis type 1 (Nf1) and myeloperoxidase (Mpo) has been reported previously in Buchberg, et al. (1988) *Oncogene Res.* 2:149–165; and Buchberg, et al. (1989) *Genetics* 122:153–161. The position of two other loci, Scya1 and Scya2, used to position Scya10 on the Frederick interspecific backcross map, have not been reported previously. The ~700 bp Scya1 and ~700 bp Scya2 mouse cDNA probes were labeled with [$\alpha$-$^{32}$P] dCTP by random priming; washing was done to a final stringency of 0.5×SSCP, 0.1% SDS, 65° C. Two Scya1 fragments, 10.5 and 0.5 kb in size, were detected in EcoRI-digested C57BL/6J DNA while 3.3 and 0.5 kb fragments were detected in EcoRI-digested *M. spretus* DNA. In addition, a 1.6 kb Scya1 fragment was detected in PstI-digested C57BL/6J DNA while 2.6 and 1.6 kb fragments were detected in PstI-digested *M. spretus* DNA. The presence or absence of the 3.3 kb *M. spretus*-specific EcoRI fragment and the 2.6 kb *M. spretus*-specific PstI fragment, which cosegregated, was followed in backcross mice. The two sets of data were combined to determine the map location of Scyal. Likewise, a major 5.5 kb Scya2 fragments was detected in TaqI-digested C57BL/6J DNA, while intensely hybridizing 7.4 and 6.3 kb Scya2 fragments were detected in *M. spretus* DNA. The presence or absence of the 7.4 and 6.3 kb *M. spretus*-specific TaqI fragments was followed in backcross mice. Backcross mice either inherited the 7.4 kb or 6.3 kb TaqI fragment but never both. This result indicates that the *M. spretus* mice used to generate the Frederick interspecific backcross were still segregating for two Scya2 alleles. Recombination distances were calculated as described in Green (1981) "Linkage, recombination and mappings", *Genetics and Probability in Animal Breeding Experiments* Oxford University Press, NY, 77, using the computer program SPRETUS MADNESS. Gene order was determined by minimizing the number of double and multiple recombination events across the chromosome.

The murine chromosomal location of CCF18 (designated gene symbol Scya10 for small inducible cytokine a10), determined by interspecific backcross analysis C57BL/6J and *M. spretus* DNAs were digested with several enzymes and analyzed by Southern blot hybridization for informative restriction fragment length polymorphisms (RFLPs) using a mouse Scya10 cDNA probe. The 5.1 kb *M. spretus*-specific BamHI fragment was used to follow the segregation of the Scya10 locus in backcross DNAs. The mapping results indicated that Scya10 is located in the middle region of mouse chromosome 11 tightly linked to two other members of the C—C chemokine family, Scya1 (Tca3) and Scya2 (Je). Although 55 mice were analyzed for five markers in the haplotype analysis, up to 134 mice were analyzed for some pairs of markers. Each locus was analyzed in pairwise combinations for recombination frequencies using the additional data. The ratios of the total number of mice exhibiting recombinant chromosomes to the total number of mice analyzed for each pair of loci and the most likely gene order are: centromere-Nf1-5134-scya1-0/107-scya10-0/98-Scya2-2/113-Mpo. The recombination frequencies [expressed as genetic distances in centiMorgans (cM)+the standard error] are centromere–Nf1–3.7+1.6–(Scya1, Scya10, Scya2)–1.8+1.2–Mpo. No recombinants were detected between Scya1 and Scya10 in 107 animals typed in common or between Scya10 and Scya2 in 98 mice typed in common suggesting that the loci in each pair are within 2.2 and 3 cM of each other (95% confidence limit), respectively.

Three other C—C chemokine genes have recently been mapped in the vicinity of Scya10. These include MIP-1α (Scya3), MIP-1β (Scya4), and RANTES (Scya5). Scya5 did not recombine with Scya1, Scya2, and Scya10; Scya3 and Scya4 did not recombine with each other in 189 animals typed in common and the two genes map 0.6+/−0.6 cM distal of the Scya10 gene cluster. These results confirm and extend the earlier observations that all C—C chemokine genes map to the central region of mouse chromosome 11. See, Wilson, et al. (1990) *J. Exp. Med.* 171:1301–1314; Berger, et al. (1993) *DNA and Cell Biol.* 12:839–847; and Danoff, et al. (1994) *J. Immunol.* 152:1182–1189.

Finally, the middle region of mouse chromosome 11 shares a region of homology with human chromosome 17q. In particular, SCYA1 and SCYA2 have been mapped to human 17q12 and 17q11.2–q12, respectively. This suggests that the human homolog of CCF18 (the Scya10 locus) should map to 17q11–q12, as well.

IV. Assays for Chemotactic Activity.

To obtain the CCF18 protein, COS cells were transfected with a plasmid carrying the CCF18 cDNA by electroporation. See, Hara, et al. (1992) *EMBO J.* 10:1875–1884. Three days after transfection, a culture supernatant was collected and subjected to bioassays. As a mock control, a plasmid carrying the luciferase cDNA was used. See, de Wet, et al. (1987) *Mol. Cell. Biol.* 7:725–737. Recombinant murine MIP-1α was purchased from R&D Systems (Minneapolis, Minn.).

Lymphocyte migration assays were performed as previously described in Bacon, et al. (1988) *Br. J. Pharmacol.* 95:966–974 with the modification that optimal migration was observed only after 2 hours incubation of the assay. Two murine Th2 T cell clones, CDC-25 (see Tony, et al. (1985) *J. Exp. Med.* 161:223–241) and HDK-1 (see Cherwinski, et al. (1987) *J. Exp. Med.* 166:1229–1248) were kindly provided by R. Coffman and A. O'Garra (DNAX, Palo Alto, Calif.), respectively. Ca2+ flux upon chemokine stimulation was measured according to the published procedure described in Bacon, et al. (1995) *J. Immunol.* 154:3654–3666.

Maximal numbers of migrating cells in response to MIP-1α occured at a concentration of $10^{-8}$ M, in agreement with original reports for CD4+ populations of human T cells. See Schall (1993) *J. Exp. Med.* 177:1821–1826. The murine T cell clones responded to both CCF18 and MIP-1α with similar maximal cell numbers, giving a characteristic bell shaped dose-response curve. A maximum number of the T lymphocytes migrated in the presence of a 500–1000 fold dilution of the CCF18 containing supernatant. At higher concentrations of CCF18, the cells adhered to the upper surface of the filter, accounting for the lower number of cells recorded on the undersurface. In all experiments the same concentration range of mock supernatant was tested but failed to have any effect on the cells. Assay for chemotactic versus chemokinetic activity demonstrated that CCF18 elicited chemotactic migration.

After stimulation with C—C chemokines, lymphocytes generally show a measurable intracellular Ca2+ flux. This was also the case with CCF18. Both MIP-1α and CCF18 were capable of inducing immediate transients of calcium mobilization. However, MIP-1α completely desensitized the cells to subsequent administration of CCF18. Prior administration of CCF18 only partially desensitized the response to subsequent administration of MIP-1α as evidenced by the smaller calcium flux profile.

The levels of CCF18 used in these assays were similar to those used for the chemotaxis assays (1/1000 dilution of conditioned supernatants). In all instances, the control COS supernatants (mock transfected) failed to elicit any calcium mobilization response.

V. Northern Blot Analysis of Mouse CCF18

RNA blot and hybridization was performed according to the standard method in Maniatis, et al. (1982) *Molecular Cloning: A Laboratory Manual* Cold Spring Harbor Laboratory Press, Cold Spring Harbor, N.Y., by using an 1.1 kb EcoRI/NotI CCF18 cDNA fragment as a probe. To verify the amount of RNA loaded in each lane, the membrane was reprobed with WAF1 cDNA, see El-Deiry, et al. (1993) *Cell* 75:817–825, which was obtained during screening of the cDNA library in this study, or glyceraldehyde 3-phosphate dehydrogenase (G3PDH) cDNA (Clontech, Palo Alto Calif.).

The CCF18 mRNA (approximately 1.4 kb in size for the major band) was constitutively expressed at a relatively high level in a macrophage cell line, P388D1, and an IL-3-dependent myeloid cell line, 32D. A small amount of CCF18 mRNA was also detected in an IL-3-dependent mast cell line, MC/9, a preB cell line, Y16, and a fibroblastic cell line, NIH3T3. However, a T-cell line, CTLL-2, and the proB line, Ba/F3, do not express CCF18 mRNA. In addition, the expression level of CCF18 mRNA in Ba/F3 cells varied from clone to clone. In BF-EGFR/EPORH, CCF18 mRNA was detected at highest and constitutively expressed without cytokine stimulation, whereas in other Ba/F3 transfectants, 626 and BF-EGFR, the amount of the CCF18 transcript was low and appeared to be cytokine-inducible in 626 cells. A cDNA encoding p21 WAF1, whose mRNA expression is enhanced by cytokine stimulation, was used to verify the RNA amount and cytokine-response in those cell lines. Thus, it is not clear how the production of CCF18 is regulated because the expression of the C—C chemokines appears to be differentially regulated by a variety of stimuli. See, Orlofsky (1994) *J. Immunol.* 152:5084–5091.

VI. Isolation of Human Chemokine Receptor, CC CKR3, cDNA

The CC CKR3 cDNA was isolated using the procedure described in Neote, et al. (1993) *Cell* 72:415–425. Two degenerate PCR primers were designed using sequences from the conserved regions of known chemokine receptors. These primers were used to amplify specific regions of human genomic DNA.

Degenerate PCR Primers

1. DRYLAIVHAdeg(+)
   5'-GAT CGI TAG CTI GCI ATI; GTI CA(T/C) GC-3'
2. TM7deg(−)α
   5'-CG GAA III (C/A)TC IC(G/C) IAC (G/A)AA IGC(G/A)TA-3' I represents deoxyinosine.

Of the DNA sequences identified by this method, one represented a portion of the CC CKR3 gene. This DNA fragment was then used to screen a Th0 activated T cell cDNA library provided by T. McClanahan (DNAX, Palo Alto Calif.), in order to obtain the full length cDNA.

VII. Generation of Antibodies to CCF18 and CC CRK3

The purified protein or defined peptides are useful for generating antibodies by standard methods, as described above. Synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. The binding reagent is either labeled as described above, e.g., fluorescence or otherwise, or immobilized to a substrate for panning methods.

The binding composition is used for screening of an expression library made from a cell line which expresses a CCF18 chemokine. Standard staining techniques are used to detect or sort intracellular or surface expressed ligand, or surface expressing transformed cells are screened by panning. Screening of intracellular expression is performed by various staining or immunofluorescence procedures. See also, e.g., McMahan, et al. (1991) *EMBO J.* 10:2821–2832.

For example, on day 0, precoat 2-chamber permanox slides with 1 ml per chamber of fibronectin, 10 ng/ml in PBS, for 30 min at room temperature. Rinse once with PBS. Then plate COS cells at $2–3\times10^5$ cells per chamber in 1.5 ml of growth media. Incubate overnight at 37° C.

On day 1 for each sample, prepare 0.5 ml of a solution of 66 μg/ml DEAE-dextran, 66 pM chloroquine, and 4 μg DNA in serum free DME. For each set, a positive control is prepared, e.g., of huIL-10-FLAG cDNA at 1 and 1/200 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80° C. after all liquid is removed. For each chamber, 0.5 ml incubations are performed as follows. Add HBSS/saponin(0.1%) with 32 μl/ml of 1M NaN3 for 20 min. Cells are then washed with HBSS/saponin 1×. Add antibody complex to cells and incubate for 30 min. Wash cells twice with HBSS/saponin. Add second antibody, e.g., Vector anti-mouse antibody, at 1/200 dilution, and incubate for 30 min. Prepare ELISA solution, e.g., Vector Elite ABC horseradish peroxidase solution, and preincubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of $H_2O_2$ per 5 ml of glass distilled water. Carefully remove chamber and rinse slide in water. Air dry for a few minutes, then add 1 drop of Crystal Mount and a cover slip. Bake for 5 min at 85–90° C.

Alternatively, the binding compositions are used to affinity purify or sort out cells expressing the ligand. See, e.g., Sambrook, et al. or Ausubel et al.

Many mocification an variations of this invention can be made without departing from its spirit and scope, as will be apparent to those skilled in the art. The specific embodiments described herein are offered by way of example only, and the invention is to be limited only by the terms of the appended claims, along with the full scope of the equivalents to which such claims are entitled.

Sequence Submission

SEQ ID NO: 1 is mouse CCF18 nucleotide sequence.
SEQ ID NO: 2 is mouse CCF18 amino acid sequence.
SEQ ID NO: 3 is human CCF18 nucleotide sequence.
SEQ ID NO: 4 is human CCF18 amino acid sequence.
SEQ ID NO: 5 is human CCKR3 nucleotide sequence.
SEQ ID NO: 6 is human CCRK3 amino acid sequence.
SEQ ID NO: 7 is a primer.
SEQ ID NO: 8 is a primer.

What is claimed is:

1. A complex comprising a CCF18 polypeptide comprising an amino acid sequence set forth in SEQ ID NO: 4 bound to an antibody that recognizes said polypeptide.

2. The complex of claim 1, wherein said CCF18chemokine:

a) exhibits a post-translational modification pattern distinct from a natural CCF18 chemokine; or b) is a mature protein of 101 amino acid residues; has four cysteine residues; has a molecular weight of about 11549 daltons; and has one potential N-glycosylation site.

3. The complex of claim 2, wherein:

a) said antibody is a monoclonal antibody; or b) said antibody is labeled.

4. A complex comprising a monoclonal antibody bound to a polypeptide comprising an amino acid sequence of SEQ ID NO: 4.

5. A method for making an antibody that recognizes a polypeptide comprising an amino acid sequence set forth in SEQ ID NO: 4 comprising immunizing an animal with the polypeptide and generating hybridoma cells with spleen cells from said animal.

6. The method of claim 5 further comprising isolating the antibody from the hybridoma.

7. A method for making an antibody that recognizes a polypeptide comprising an amino acid sequence set forth in SEQ ID NO: 4 comprising immunizing an animal with the polypeptide.

8. The method of claim 7 further comprising isolating the antibody from the animal.

* * * * *